US012745915B2

(12) United States Patent
Pfeiffer et al.

(10) Patent No.: US 12,745,915 B2
(45) Date of Patent: Sep. 29, 2026

(54) APPARATUS FOR DETERMINING AN INDICATOR REPRESENTATIVE FOR A PHYSIOLOGICAL PARAMETER

(71) Applicant: KONINKLIJKE PHILIPS N.V., Eindhoven (NL)

(72) Inventors: Ulrich Pfeiffer, Boeblingen (DE); Benjamin Stolze, Taufkirchen (DE); Stephan Guido Maria Regh, Boeblingen (DE); Antonia Kiefer, Boeblingen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 162 days.

(21) Appl. No.: 18/852,948

(22) PCT Filed: Mar. 24, 2023

(86) PCT No.: PCT/EP2023/057696
§ 371 (c)(1),
(2) Date: Sep. 30, 2024

(87) PCT Pub. No.: WO2023/186745
PCT Pub. Date: Oct. 5, 2023

(65) Prior Publication Data

US 2025/0213120 A1 Jul. 3, 2025

(30) Foreign Application Priority Data

Mar. 30, 2022 (EP) .................................... 22165329

(51) Int. Cl.
*A61B 5/0205* (2006.01)
*A61B 5/022* (2006.01)
(Continued)

(52) U.S. Cl.
CPC ............ *A61B 5/0205* (2013.01); *A61B 5/022* (2013.01); *A61B 5/02444* (2013.01); *A61B 5/0816* (2013.01); *A61B 2562/0247* (2013.01)

(58) Field of Classification Search
CPC ... A61B 5/0205; A61B 5/022; A61B 5/02444; A61B 5/0816; A61B 2562/0247
(Continued)

(56) References Cited

U.S. PATENT DOCUMENTS 5,752,919 A * 5/1998 Schrimpf ............ A61B 5/7207 600/494
6,767,328 B2 * 7/2004 Kulik ................ A61B 5/02225 600/494
(Continued)

FOREIGN PATENT DOCUMENTS

EP 2759257 A1 * 7/2014 .......... A61B 5/7278
EP 2759257 B1 9/2016
(Continued)

OTHER PUBLICATIONS

International Search Report Dated Jun. 23, 2023 For International Appln No. PCT/EP2023/057696 Filed Mar. 24, 2023.

*Primary Examiner* — Michael Tomaszewski
(74) *Attorney, Agent, or Firm* — Brynne J. Corcoran

(57) ABSTRACT

The invention relates to an apparatus for determining an indicator, which is representative for a physiological parameter of a patient like a fluid responsiveness parameter, based on a pulse signal. The apparatus determines a) a respiratory pulse variation signal (r0) corresponding to pulse variations caused by ventilation or respiration induced heart-lung interaction based on the pulse signal and b) a systolic part of the respiratory pulse variation signal, which corresponds to a time period in which an increasing or decreasing applied pressure passed the systolic arterial pressure of the patient and which therefore is prone to comprising an artifact.
(Continued)

Moreover, the respiratory pulse variation signal is modified such that the determined systolic part of the respiratory pulse variation signal is corrected, wherein the indicator is determined based on the measured pulse signal and the modified respiratory pulse variation signal. This procedure allows for a more accurate determination of the indicator.

19 Claims, 6 Drawing Sheets

(51) Int. Cl.
*A61B 5/024* (2006.01)
*A61B 5/08* (2006.01)

(58) Field of Classification Search
USPC .......................................................... 600/301
See application file for complete search history.

(56) References Cited

U.S. PATENT DOCUMENTS

| | | | | |
|---|---|---|---|---|
| 6,776,764 | B2 * | 8/2004 | Pinsky | A61B 5/02007 600/301 |
| 8,992,431 | B2 * | 3/2015 | Merilainen | A61B 5/02116 600/490 |
| 2004/0024323 | A1 * | 2/2004 | Kulik | A61B 5/02225 600/490 |
| 2004/0249297 | A1 * | 12/2004 | Pfeiffer | A61B 5/0205 600/526 |
| 2007/0073170 | A1 * | 3/2007 | Danehorn | A61B 5/0205 600/484 |
| 2010/0324428 | A1 * | 12/2010 | Pfeiffer | A61B 5/02233 600/490 |
| 2011/0009756 | A1 * | 1/2011 | Merilainen | A61B 5/02116 600/490 |
| 2012/0029361 | A1 * | 2/2012 | Addison | A61B 5/02125 600/484 |
| 2013/0053664 | A1 * | 2/2013 | Jian | A61B 5/0205 600/324 |
| 2014/0207004 | A1 * | 7/2014 | Addison | A61B 8/00 600/484 |
| 2015/0157269 | A1 * | 6/2015 | Lisogurski | A61B 5/6838 600/301 |
| 2020/0367764 | A1 * | 11/2020 | Le Guillou | A61B 5/7207 |
| 2025/0213120 | A1 * | 7/2025 | Pfeiffer | A61B 5/0205 |
| 2026/0013740 | A1 * | 1/2026 | Stolze | A61B 5/021 |

FOREIGN PATENT DOCUMENTS

| | | | |
|---|---|---|---|
| WO | 2014121945 | A1 | 8/2014 |
| WO | 2017129495 | A1 | 8/2017 |

* cited by examiner

APPARATUS FOR DETERMINING AN INDICATOR REPRESENTATIVE FOR A PHYSIOLOGICAL PARAMETER

CROSS-REFERENCE TO PRIOR APPLICATIONS

This application is the U.S. National Phase application under 35 U.S.C. § 371 of International Application No. PCT/EP2023/057696 filed on Mar. 24, 2023, which claims the benefit of International application Ser. No. 22/165,329.8 filed on Mar. 30, 2022. These applications are hereby incorporated by reference herein.

FIELD OF THE INVENTION

The invention relates to an apparatus, a method and a computer program for determining an indicator that is representative for a physiological parameter.

BACKGROUND OF THE INVENTION

EP 2 759 257 B1 discloses a method for determining an indicator that is representative for a patient's volume responsiveness. A pulse signal of a patient over a time period corresponding to a plurality of subsequent respiratory cycles of the patient is measured, wherein the measured pulse signal is detected by a non-invasive pulse measurement method using a pressure cuff, wherein the pressure applied in the pressure cuff is continuously increased or decreased in the course of a measurement period. The measured pulse signal is represented as pulse signal oscillating around an average value thereof, wherein an envelope signal curve for the pulse signal is determined. Moreover, a fit envelope signal function is determined based on the previously determined envelope signal curve, wherein the fit envelope signal function is determined based on a predetermined first functional prototype and represents an idealized curve progression of the envelope signal curve over the plurality of respiratory cycles without comprising pulse variations caused by ventilation or respiration induced heart-lung interaction. Then, a respiratory pulse variation signal is determined, which corresponds to the pulse variations caused by ventilation or respiration induced heart-lung interaction over the plurality of respiratory cycles, wherein the determined respiratory pulse variation signal corresponds to a difference between the envelope signal curve and the fit envelope signal function. As a next step, an envelope respiration curve is determined for the previously determined respiratory pulse variation signal and a fit envelope respiration function is determined based on the previously determined envelope respiration curve, wherein the fit envelope respiration function is determined based on a predetermined second functional prototype and represents an idealized curve progression of the envelope respiration curve over the plurality of respiratory cycles. Finally, the indicator that is representative for the patient's volume responsiveness is determined based on the fit envelope signal function and the fit envelope respiration function.

SUMMARY OF THE INVENTION

It is an object of the present invention to provide an apparatus, a method and a computer program which allow for an improved determination of an indicator that is representative for a physiological parameter.

In a first aspect of the present invention an apparatus for determining an indicator that is representative for a physiological parameter is presented, wherein the apparatus comprises:

a pulse signal providing unit configured to provide a measured pulse signal of a patient over a time period corresponding to a plurality of subsequent respiratory cycles of the patient, wherein the pulse signal is a pressure signal that has been measured by using a pressure cuff with a pressure sensor being in contact with the outer skin of the patient, wherein pressure applied to the patient by the pressure cuff is increased or decreased, while the pressure sensor measures the pressure signal on the outer skin of the patient, and wherein the measured pressure is indicative of blood pulsations, an indicator determination unit configured to carry out a determination procedure adapted to determine an indicator that is representative for a physiological parameter based on the provided pulse signal, wherein the determination procedure includes a) determining a respiratory pulse variation signal corresponding to pulse variations caused by ventilation or respiration induced heart-lung interaction based on the provided measured pulse signal, b) determining a systolic part of the respiratory pulse variation signal, which corresponds to a time period in which the increasing or decreasing applied pressure passed the systolic arterial pressure of the patient and which therefore is prone to comprising an artifact, c) modifying the respiratory pulse variation signal such that the determined systolic part of the respiratory pulse variation signal is corrected and d) determining the indicator based on the measured pulse signal and the modified respiratory pulse variation signal.

When the pressure applied to the patient by using the pressure cuff, which also might be regarded as being a clamping pressure, is increased or decreased, particularly continuously increased or decreased, it will pass the systolic arterial pressure of the patient at least once depending on the heart-lung interaction. If the heart-lung interaction is large leading to high systolic arterial pressure variation, there can be several passings of the clamping pressure with the systolic arterial pressure.

During these passings of clamping pressure with systolic arterial pressure mostly a sudden, significant change in pressure pulses' amplitudes and/or areas under pressure pulse curves, i.e. the amplitudes and/or areas under the pressure pulse curves of the measured pulse signal, can occur with the amplitudes and/or the areas under the curves becoming smaller during clamping pressure increase or larger during clamping pressure decrease. This can affect the respiratory pulse variation signal which is determined based on the measured pulse signal, i.e. it can introduce artifacts falsifying the respiratory pulse variation signal, which finally could lead to inaccuracies in determining the indicator that is representative for the physiological parameter. However, this adverse effect can be overcome or at least reduced by determining a systolic part of the respiratory pulse variation signal, which corresponds to a time period in which the increasing or decreasing applied pressure passed the systolic arterial pressure of the patient, and by modifying the respiratory pulse variation signal such that the determined systolic part of the respiratory pulse variation signal is corrected.

The physiological parameter is preferentially a physiological parameter of a patient. Preferably, the physiological parameter is indicative of, or corresponds to, a patient's volume or fluid responsiveness. Accordingly, the determination of the indicator that is representative for the physiological parameter is preferentially a determination of a fluid responsiveness parameter (FRP), especially of a pulse pressure variation (PPV), a systolic pressure variation (SPV) and/or a stroke volume variation (SVV). In these particular cases, the determined indicator may be the respective FRP, i.e. a PPV, an SPV and/or an SVV. The physiological parameter can also be indicative of, or correspond to, for instance, a blood pressure, such as an arterial blood pressure. Accordingly, the determination of the indicator that is representative for the physiological parameter can also be a determination of one or more parameters related to the blood pressure. Then, the determined indicator can be the respective parameter related to the blood pressure.

The provision of the measured pulse signal, which comprises a sequence of pulses, can correspond to measuring the pulse signal of the patient, particularly to measuring a signal corresponding to blood pulsations by continuously or semi-continuously recording the pressure indicative of the blood pulsations. In an embodiment the measured pulse signal has been detected by a non-invasive pulse measurement method using a pressure cuff, wherein the pressure applied in the pressure cuff is continuously increased or decreased in the course of a measurement period and wherein the pressure cuff comprises the pressure sensor being in contact with the outer skin of the patient for measuring the pressure, which could be named tissue pressure and which is indicative of the blood pulsations.

The pressure sensor can be in direct contact with the outer skin or in indirect contact with the outer skin. In the latter case there are one or several intermediate elements between the outer skin and the pressure sensor, which transfer the tissue pressure from the outer skin to the pressure sensor. The intermediate elements can be solid or fluid elements. Preferably, the pulse signal with the sequence of pulses is measured using a pressure cuff that is adapted to provide a hydraulic coupling between blood pulsations and a pressure sensor of the pressure cuff that is adapted to record the pressure indicative of the blood pulsations. A pressure cuff of this kind is disclosed, for instance, in WO 2014/121945 A1. Using such a pressure cuff, which will subsequently be referred to also as a high-fidelity pressure cuff, allows for an improved quality of the recorded pressure signal as compared to, for instance, oscillometric measurements relying on a pneumatic coupling. As mentioned above, the pressure cuff may be adapted to bring the pressure sensor into direct contact with the patient's tissue such that it is hydraulically coupled to blood pulsations via the tissue. The pressure cuff may, for instance, be a high-fidelity upper arm pressure cuff.

The provision of the pulse signal may also comprise a providing of a pulse signal which has been measured previously by, for instance, a physician. The measured pulse signal may hereafter have been stored and this stored pulse signal might be provided.

In an embodiment, the indicator determination unit is configured to correct the systolic part of the respiratory pulse variation signal by replacing at least a subpart of the systolic part by another part of the respiratory pulse variation signal and/or by removing at least a subpart of the systolic part. In particular, in a preferred embodiment the indicator determination unit is configured to correct the systolic part of the respiratory pulse variation signal by replacing the systolic part by another part, particularly an adjacent part, of the respiratory pulse variation signal. Moreover, the indicator determination unit preferentially is configured to determine the systolic part of the respiratory pulse variation signal such that it consists of half waves of the respiratory pulse variation signal. A half wave preferentially is defined as a part of the respiratory pulse variation signal above or below an average value of the respiratory pulse variation signal, wherein the start point of the part and the end point of the part are subsequent points of intersection of the respiratory pulse variation signal with a line representing the average value. It has been found that a modification of the respiratory pulse variation signal in this way allows for a further improved determination of the indicator being representative of the physiological parameter.

Preferentially, the indicator determination unit is configured to represent the respiratory pulse variation signal as a respiratory pulse variation signal oscillating around an average value thereof and to determine the systolic part of the respiratory pulse variation signal such that it includes a lowest minimum and/or a highest maximum of the respiratory pulse variation signal. Thus, the indicator determination unit can be configured to determine the lowest minimum and/or the highest maximum of the respiratory pulse variation signal and to determine the systolic part of the respiratory pulse variation signal such that it includes the determined lowest minimum and/or the determined highest maximum of the respiratory pulse variation signal.

In particular, the indicator determination unit is configured to determine the systolic part of the respiratory pulse variation signal such that it includes a half wave of the respiratory pulse variation signal with a lowest minimum and/or a half wave of the respiratory pulse variation signal with a highest maximum and to modify the respiratory pulse variation signal by a) replacing the lowest minimum half wave and/or the highest maximum half wave by a half wave of another part of the respiratory pulse variation signal and/or b) removing the lowest minimum half wave and/or the highest maximum half wave. In a preferred embodiment, the indicator determination unit is configured to determine the systolic part of the respiratory pulse variation signal such that it includes at least one first half wave of the respiratory pulse variation signal adjacent the half wave of the respiratory pulse variation signal with the lowest minimum and/or at least one second half wave of the respiratory pulse variation signal adjacent the half wave of the respiratory pulse variation signal with the highest maximum and to modify the respiratory pulse variation signal by a) replacing the at least one first half wave and/or the at least one second half wave by a half wave of another part the respiratory pulse variation signal and/or b) removing the at least one first half wave and/or the at least one second half wave.

In particular, the indicator determination unit can be configured to determine the systolic part of the respiratory pulse variation signal such that it includes a half wave of the respiratory pulse variation signal with a lowest minimum and to modify the respiratory pulse variation signal by replacing the determined lowest minimum half wave by an adjacent half wave of the respiratory pulse variation signal. In a preferred embodiment, the indicator determination unit is configured to determine the systolic part of the respiratory pulse variation signal such that it further includes a half wave of the respiratory pulse variation signal with a highest maximum and to modify the respiratory pulse variation signal by replacing the temporally first one of the lowest minimum half wave and the highest maximum half wave by a half wave before and adjacent to the first one and replacing the respective temporally second one of the lowest minimum half wave and the highest maximum half wave by a half wave behind and adjacent to the temporally second one. The half waves with artifacts will usually have an enlarged amplitude due to the artifact falsifying the respiratory pulse variation signal when clamping pressure is passing systolic arterial pressure. This can falsify positive and negative half waves of the respiratory pulse variation signal. Therefore, intention of removing the half wave with the lowest minimum and the half wave with the highest maximum is to remove the influence of this artefact. Intention of replacing the half waves is to fill the gaps in the data allowing, for instance, for a more appropriate fitting of the respiratory pulse variation signal.

In a further embodiment the indicator determination unit is configured to determine the systolic part of the respiratory pulse variation signal such that it further includes the half wave before and adjacent to the lowest minimum half wave and to modify the respiratory pulse variation signal by replacing the lowest minimum half wave by a half wave behind and adjacent to the lowest minimum half wave and replacing the half wave before and adjacent to the lowest minimum half wave by a half wave before and adjacent to this half wave to be replaced. As mentioned above, the half waves with artifacts will usually have an enlarged amplitude due to the artifact falsifying the respiratory pulse variation signal when clamping pressure is passing systolic arterial pressure. Often a negative half wave and its previous positive half wave of the respiratory pulse variation signal are falsified. Therefore, intention of removing the half wave with the lowest minimum and the previous half wave is to remove the influence of this artefact. Intention of replacing the half waves is to fill the gaps in the data allowing, for instance, for a more appropriate fitting of the respiratory pulse variation signal.

It is noted that terms like “before”, “behind”, “previous”, “subsequent”, et cetera refer to the direction of increasing applied pressure. In other words, if the applied pressure increases, for instance the term “before” corresponds to temporally earlier and the term “behind” corresponds to temporally later and, if the applied pressure decreases, for instance the term “before” corresponds to temporally later and the term “behind” corresponds to temporally earlier.

In an example, the indicator determination unit is configured to determine the systolic part of the respiratory pulse variation signal as a part in which a maximum decrease position is present, at which the respiratory pulse variation signal and/or an envelope signal curve of the pulse signal has its maximum decrease. Determining the systolic part of the respiratory pulse variation signal as the part in which the maximum decrease position is present allows to determine the systolic part with a further increased accuracy.

The maximum decrease position is preferentially the position at which the decrease is globally maximal. The maximum decrease position at which the respiratory pulse variation signal and/or the envelope signal curve has its maximum decrease can also be regarded as being a minimum negative slope position, because at the maximum decrease position the negative slope of the respiratory pulse variation signal and/or of the envelope signal curve has its smallest negative value.

Thus, the indicator determination unit can be configured to determine several decreases along the respiratory pulse variation signal and/or along the envelope signal curve and to then determine the position along the respiratory pulse variation signal and/or the envelope signal curve, respectively, at which the maximum decrease is present, in order to determine the systolic part of the respiratory pulse variation signal.

The width of the determined systolic part of the respiratory pulse variation signal is preferentially defined by two adjacent half waves that, in the previously described example, include the maximum decrease position. Also in other embodiments and examples of determining the systolic part of the respiratory pulse variation signal this systolic part preferentially has a width defined by two adjacent half waves.

The maximum decrease can be determined as the maximum decrease of the respiratory pulse variation signal when it is represented as a respiratory pulse variation signal oscillating around an average value thereof or when the respiratory pulse variation signal is not represented as a respiratory pulse variation signal oscillating around the average value thereof. Correspondingly, the maximum decrease can be determined as the maximum decrease of the envelope signal curve of the pulse signal when it is represented as a pulse signal oscillating around an average value thereof or when it is not represented as a pulse signal oscillating around the average value thereof.

In an example, the envelope signal curve is a smooth curve outlining the extremes in amplitude of the pulse signal. Preferentially, the pulse signal is represented as a pulse signal oscillating around the average value thereof, wherein, in order to determine the envelope signal curve, the portions of the pulse signal below the average value of the oscillating pulse signal are folded up to the upper portions and then a smooth curve outlining the resulting sequence of maxima is determined as the envelope signal curve. More details regarding possible determinations of the envelope signal curve are described further below.

In an example, the indicator determination unit is configured to represent the respiratory pulse variation signal as a respiratory pulse variation signal oscillating around an average value thereof and to modify the respiratory pulse variation signal by a) replacing the half wave, which comprises the maximum immediately before the maximum decrease position, of the respiratory pulse variation signal and the half wave, which comprises the minimum immediately behind the maximum decrease position, of the respiratory pulse variation signal by half waves of another part the respiratory pulse variation signal and/or b) removing these half waves. Thus, in this example the systolic part of the respiratory pulse variation signal is defined by two half waves, wherein the two half waves include a first half wave having a maximum immediately before the maximum decrease position and a second half wave having a minimum immediately behind the maximum decrease position. Replacing these half waves by other half waves and/or removing these half waves provides an improved respiratory pulse variation signal that can be used to determine the indicator, which is representative for a physiological parameter, even more accurately.

If the correction of the respiratory pulse variation signal is carried out by replacement, in an example the first half wave, which comprises the maximum immediately before the maximum decrease position, is replaced by the half wave of the respiratory pulse variation signal, which is immediately before the first half wave, and the second half wave, which comprises the minimum immediately behind the maximum decrease position, is replaced by the half wave of the respiratory pulse variation signal immediately behind this second half wave.

In an example the indicator determination unit is configured to determine the systolic part of the respiratory pulse variation signal as a part in which a difference between two consecutive extrema of the respiratory pulse variation signal is largest. The two consecutive extrema of the respiratory pulse variation signal can be a maximum and a following minimum or a minimum and a following maximum. However, preferentially the two consecutive extrema are a maximum and a following minimum. Thus, in an embodiment, the indicator determination unit is configured to determine the systolic part of the respiratory pulse variation signal as a part in which a difference between a maximum of the respiratory pulse variation signal and a directly following minimum of the respiratory pulse variation signal is largest.

Preferentially, the determined systolic part of the respiratory pulse variation signal has a width of two half waves, as also explained above. Thus, in an embodiment, the respiratory pulse variation signal is defined by the half wave of the respiratory pulse variation signal and the following half wave of the respiratory pulse variation signal for which the difference between a maximum and the directly following minimum is largest.

Hence, the indicator determination unit can be configured to determine differences between respective two consecutive extrema of the respiratory pulse variation signal and then determine which of these differences is largest, in order to determine the systolic part of the respiratory pulse variation signal as a part in which the difference between two consecutive extrema of the respiratory pulse variation signal is largest. Preferentially, as indicated above, the indicator determination unit determines differences between a maximum and a directly following minimum of the respiratory pulse variation signal for the corresponding pairs maximum-minimum of the respiratory pulse variation signal and determines which of these differences is largest, in order to determine the systolic part of the respiratory pulse variation signal as a part in which the difference between a maximum and a following minimum of the respiratory pulse variation signal is largest.

In an example the indicator determination unit is configured to represent the respiratory pulse variation signal as a respiratory pulse variation signal oscillating around an average value thereof and to modify the respiratory pulse variation signal by a) replacing the half waves, which comprise the consecutive extrema with the largest difference by half waves of another part the respiratory pulse variation signal and/or b) removing these half waves. Thus, in an example, the systolic part of the respiratory pulse variation signal can be defined by two half waves, wherein the two half waves include the two consecutive extrema with the largest difference, wherein in a preferred embodiment the indicator determination unit considers as consecutive extrema a respective maximum followed by a respective minimum, but not a respective minimum followed by a respective maximum. Replacing these half waves by other half waves and/or removing these half waves provides an improved respiratory pulse variation signal that can be used to determine the indicator, which is representative for a physiological parameter, even more accurately.

Also in this example, if the correction of the respiratory pulse variation signal is carried out by replacement, preferentially the first half wave, which comprises the first extremum being preferentially a maximum, is replaced by the half wave of the respiratory pulse variation signal, which is immediately before this first half wave, and the second half wave, which comprises the second extremum being preferentially the following minimum, is replaced by the half wave of the respiratory pulse variation signal immediately behind the second half wave.

It is preferred that the pulse signal providing unit is configured to represent the measured pulse signal as pulse signal oscillating around an average value thereof, wherein the indicator determination unit is configured to represent the respiratory pulse variation signal as a respiratory pulse variation signal oscillating around an average value thereof and to represent the modified respiratory pulse variation signal as a modified respiratory pulse variation signal oscillating around an average value thereof, and wherein the indicator determination unit is configured such that

- first data values are determined by determining an envelope signal curve for the pulse signal,
- in a first fitting, a provided first functional prototype, which depends on a first fit parameter to be modified during the first fitting, is fitted to the first data values such that a resulting fit envelope signal function represents an idealized curve progression of the envelope signal curve over the plurality of respiratory cycles without comprising pulse variations caused by ventilation or respiration induced heart-lung interaction,
- second data values are determined by determining an absolute respiratory pulse variation curve for the modified respiratory pulse variation signal,
- in a second fitting, a provided second functional prototype, which depends on a second fit parameter to be modified during the second fitting, is fitted to the second data values such that a resulting fit respiration function is indicative of an idealized progression in amplitude of the absolute respiratory pulse variation curve over the plurality of respiratory cycles, and
- the indicator is determined based on the fit envelope signal function and the fit respiration function.

In particular, the indicator determination unit is configured such that the determined respiratory pulse variation signal corresponds to a difference between the envelope signal curve and the fit envelope signal function. This is particularly preferred if the measured pulse signal has been detected using a pressure cuff, wherein the pressure applied in the pressure cuff is continuously increased or decreased in the course of a measurement period.

The respective functional prototype depends on one or more respective fit parameters to be modified during fitting, wherein an initial value for each of the one or more fit parameters can be determined. The initial value for each or only some of the one or more fit parameters can be determined based on characteristics of the data values which are related to characteristics of the functional prototype and/or based on a value of the respective fit parameter known from a previous fitting. For those of the one or more fit parameters whose initial values are not determined based on characteristics of the data values which are related to characteristics of the functional prototype and/or based on a value of the respective fit parameter known from a previous fitting, the initial value might be predefined or determined based on characteristics of the measurement method, such as rate of change in pressure applied in a pressure cuff, for instance.

The respective functional prototype can be predetermined depending on an expected form of the respective data values to which the respective functional prototype should be fitted. Moreover, the respective functional prototype can also be predetermined depending on a chosen manner of determining the respective data values, wherein the chosen manner may correspond, for instance, to a defined preprocessing. For fitting the provided respective functional prototype to the respective determined data values, any known fitting algorithm may be used. Preferentially, a non-linear least squares algorithm may be used, particularly the Levenberg-Marquardt algorithm.

It is preferred that the respective functional prototype is a bell-shaped function. This is particularly preferred if the initial measured pulse signal with the several pulses has been detected using a pressure cuff, wherein the pressure applied in the pressure cuff is continuously increased or decreased in the course of a measurement period. The bell-shaped function is preferentially a Cauchy-Lorentz function. The bell-shaped function can have a fit parameter being indicative of the height of the maximum of the bell-shaped function and a further fit parameter being indicative of the position of the maximum of the bell-shaped function, wherein the indicator determination unit can be configured to determine a height of a maximum of the respective data values and a position of the maximum of the respective data values as initial values for these fit parameters.

Preferentially, the indicator determination unit is configured to determine the indicator based on a first ratio of a maximum of the fit respiration function and the maximum of the fit envelope signal function, which is named modified first ratio because of being based on the modified respiratory pulse variation signal, and/or based on a second ratio of a) the fit respiration function at the maximum of the fit envelope signal function and b) the maximum of the fit envelope signal function, which is named modified second ratio because of being based on the modified respiratory pulse variation signal. In an embodiment, the indicator determination unit is configured to carry out the steps of determining the second data values and of fitting, in the second fitting, a provided second functional prototype resulting in the fit respiration function as defined in claim 12 for the unmodified respiratory pulse variation signal and to determine the indicator also based on a second ratio of a) the fit respiration function, which has been determined based on the unmodified respiratory pulse variation signal, at the maximum of the fit envelope signal function and b) the maximum of the fit envelope signal function, which is named unmodified second ratio because of being based on the unmodified respiratory pulse variation signal, and/or based on a first ratio of a maximum of the fit respiration function, which has been determined based on the unmodified respiratory pulse variation signal, and the maximum of the fit envelope signal function, which is named unmodified first ratio because of being based on the unmodified respiratory pulse variation signal. Thus, in an embodiment, the second data value determination and second fitting steps carried out in claim 12 for the modified respiratory pulse variation signal are also carried out for the unmodified respiratory pulse variation signal.

In particular, the indicator determination unit is configured to determine the indicator based on a combination of a respective ratio and a square of a respective ratio. In a preferred embodiment, the indicator determination unit is configured to determine the indicator based on a combination of i) the first modified ratio or the second modified ratio, ii) the square of the first modified ratio or of the second modified ratio, iii) the second unmodified ratio or the first unmodified ratio, and iv) the square of the second unmodified ratio or of the first unmodified ratio. For instance, the indicator determination unit can be configured to determine the indicator by A) multiplying the square of the second unmodified ratio or of the first unmodified ratio with a first factor for calculating a first product, multiplying the second unmodified ratio or the first unmodified ratio, respectively, with a second factor for calculating a second product, adding the first and second products and a summand for calculating a first subindicator, and/or B) carrying out the steps of determining the second data values and of fitting, in the second fitting, a provided second functional prototype resulting in the fit respiration function as defined in claim 12 and carrying out the steps of determining the first modified ratio or the second modified ratio as defined in claim 14 for the respiratory pulse variation signal which has been modified as defined in claim 6, multiplying the square of the first modified ratio or of the second modified ratio, respectively, with a third factor for calculating a third product, multiplying the first modified ratio or the second modified ratio, respectively, with a fourth factor for calculating a fourth product and adding the third and fourth products and a summand for calculating a second subindicator, and/or C) carrying out the steps of determining the second data values and of fitting, in the second fitting, a provided second functional prototype resulting in the fit respiration function as defined in claim 12 and carrying out the steps of determining the first modified ratio or second modified ratio as defined in claim 14 for the respiratory pulse variation signal which has been modified as defined in claim 7, multiplying the square of the first modified ratio or the second modified ratio, respectively, with a fifth factor for calculating a fifth product, multiplying the first modified ratio or the second modified ratio, respectively, with a sixth factor for calculating a sixth product and adding the fifth and sixth products and a summand for calculating a third subindicator, and/or D) carrying out the steps of determining the second data values and of fitting, in the second fitting, a provided second functional prototype resulting in the fit respiration function as defined in claim 12 and carrying out the steps of determining the first modified ratio as defined in claim 14 for the respiratory pulse variation signal which has been modified as defined in claim 9, multiplying the square of the first modified ratio or of the second modified ratio with a seventh factor for calculating a seventh product, multiplying the first modified ratio or the second modified ratio, respectively, with an eighth factor for calculating an eighth product and adding the seventh and eighth products and a summand for calculating a fourth subindicator, and E) combining the determined subindicators. It has been found that this allows for a very accurate non-invasive determination of the indicator being representable of a physiological property like, for instance, PPV, SVV or SPV.

The different parameters, i.e. the factors and summands and also the kind of combining the subindicators, are preferentially predefined and can be predetermined by calibration measurements, wherein by invasive means reference indicators like, for instance, reference PPV, SVV and SPV are determined very accurately and the parameters are determined such that the indicator determination unit yields the very accurately invasively measured indicators with high statistical precision and accuracy. In particular, for the calibration measurement pairs of simultaneously recorded invasive and noninvasive indicator values from an adequate number of individuals of a representative population, for instance including all genders, relevant ranges of body height, weight and ages in different hemodynamic conditions are used. It should be noted that the calibration is preferentially only carried out in a development phase, i.e. not during an actual measurement procedure. The calibration can be carried out separately for different shell sizes, i.e. preferentially for different cuff sizes, or for different groups of shell sizes. For instance, for different shell sizes or groups of shell sizes, different sets of parameters can be determined by calibration, i.e. for each shell size or for each group of shell sizes a respective set of parameters can be determined.

In an embodiment the indicator determination unit is configured to carry out a respective one of steps A), B), C) and D), only if a predefined characteristic of the respective corresponding fit respiration function fulfils a respective predefined condition. For instance, if the maximum of the respective fit respiration function is smaller than a predefined threshold, or if the argument of a maximum of the respective corresponding fit respiration function is within predetermined limits. Thus, the respective fit respiration function is considered only, if it provides reasonable values, thereby allowing for a further increased accuracy of determining the indicator that is representative for a physiological parameter.

The pulse signal comprising the several pulses may be detected over a configurable time period. Preferentially, the time period is configured such that it covers a defined number of subsequent respiratory or ventilation cycles of the patient, wherein the predetermined number may be any number from one to, for instance, ten, wherein in an embodiment also more than ten subsequent respiratory or ventilation cycles might be used. For instance, the time period may be configured to have a length of between, for instance, 10 seconds and two minutes, preferably between 30 seconds and two minutes, more preferably about one minute. The pulse rate of the patient depends on various factors, such as age, stress, et cetera. The heart of an adult beats usually between 50 to 90 times per minute, when at rest. Thus, a comparatively larger number of pulse variations caused by heartbeats can be detected in the detection time period. Such an approach can be advantageous in view of the data quality underlying the calculation of the indicator representative for the physiological parameter. However, when applying a non-invasive blood pressure measurement method using a high-fidelity pressure cuff, the detection period should preferably not exceed three minutes so as to avoid adverse effects due to disturbed blood flow caused by the pressure of the pressure cuff.

The patient's respiration has a detectable influence on pulse variation. While the measured variation of the blood pressure is primarily derived from the function of the heart, i.e. from its cyclic contractions and relaxations, there is also another influential factor to be considered. Thus, two functions are superimposed: Variations of higher frequency caused by the function of the heart are superimposed by variations of lower frequency caused by the respiration or ventilation of the patient. Notably, such low frequency variations caused by the patient's respiration are not only detected with mechanically ventilated patients, but also with non-ventilated patients breathing spontaneously. Even though the effect of spontaneous breathing is somehow similar to the effect of mechanical ventilation as to variations of blood pressure, both effects are actually not the same for the following reason: In the case of mechanical ventilation, air is pressed at high pressure from outside into the lungs during inspiration, whereas, in case of spontaneous breathing, air is sucked by lower pressure into the lungs during inspiration. Irrespective of these phenomenological distinctions, in an embodiment the apparatus can be equally applied to mechanical ventilated and spontaneous breathing non-ventilated patients, provided that the respiration—or ventilation—induced maneuver produces significant heart-lung-interaction.

The measured pulse signal may be represented as a function over time or, alternatively, as a function over a clamping pressure exerted by the pressure cuff, wherein the pressure applied in the pressure cuff is continuously increased or decreased in the course of the measurement period.

The envelope signal curve, to which the first data values may correspond, is determined based on the pulse signal comprising the several pulses. Usually, an envelope curve or function of a rapidly varying signal is considered to be a smooth curve outlining the extremes in amplitude of the rapidly varying signal. For example, the envelope curve or function may be determined by simply connecting the maxima or the minima of the rapidly varying signal. However, preferentially the envelope curve of the blood pressure signal, i.e. the envelope signal curve, is determined by continuously determining a distance dimension of the measured pulse signal from an average thereof and, thereafter, preferably by applying a low pass filter to the distance dimension. Preferably, the low pass filter has a cutoff frequency below the pulse rate of the patient. For example, the portion below the average value of the oscillating curve of the measured pulse signal is preferably folded up to the upper portion. Then, the resulting curve is preferably flattened by using a low pass filter having a cutoff frequency below the pulse rate of the patient. The resulting curve can be flattened in such a way that the area below the flattened curve remains unchanged as compared to the area under the non-flattened curve. Optionally, the flattened curve may additionally be multiplied by a predetermined value. If the flattened curve is multiplied, for example, by the square root of 2, the finally obtained envelope signal curve substantially is at the level of the upper extremes in amplitude of the measured pulse signal.

The distance dimension could also be defined as the squared signal or the extreme values within a certain region, for instance, of about one pulse width or any other metric function. More generally, the distance dimension could also be defined, for instance, as the absolute value of the difference between the signal and its average value to the power of n, wherein n may be 1 or any other number. In case of using the absolute value of the difference as a distance dimension, the result correlates well with the SVV as well as the PPV. Also with the absolute value of the difference to the power of 2 as a distance dimension, the result correlates well to SVV as well as PPV. Preferably, the absolute value of the difference to the power of 2 is used as the distance dimension if the SVV is to be determined, and the absolute value of the difference is used as the distance dimension if the PPV is to be determined. With raising n, the correlation may be further increased. With the maximum metric, i.e. with infinite n as a distance dimension, the result correlates very well with PPV. For example, the maximum metric could be realized by searching the maximum value minus the minimum value of the difference within a moving window equal to the duration of a heartbeat.

The average value, which may be used as the basis of the distance dimension calculation, of the measured pulse signal can be determined as moving average over a period of one single pulse cycle of the patient or by applying a low pass filter on the measured pulse signal, e.g. an elliptic or butterworth filter. Given a series of numbers, which in this case are the pulses of the measured pulse signal, and a fixed subset size, which in this case is the period of one single pulse cycle of the patient, the first element of the moving average is obtained by taking the average of the initial fixed subset of the number series. Then the subset is modified by "shifting forward", that is excluding the first number of the series and including the next number following the original subset in the series. This creates a new subset of numbers, which is averaged. This process is repeated over the entire data series.

In some instances, it may be advantageous, in order to obtain a well-fittable envelope signal curve, to apply a window function to the measured pulse signal before determining the envelope signal curve. In particular, if the pulse signal is measured using a continuous invasive blood pressure measurement method, application of a window function is advantageous. Unlike in the above-described non-invasive blood pressure measurement method using a high-fidelity pressure cuff, a pulse signal measured by a continuous invasive blood pressure measurement method usually does not exhibit any bell-shaped form. If a pulse signal is measured using a non-invasive blood pressure measurement method employing a high-fidelity pressure cuff, application of a window function may not be required. Under such circumstances, a measured pulse of the pulse signal usually already exhibits a bell-shaped form, and, therefore, is—as such—well fittable with a functional prototype also exhibiting a bell-shaped form. If a window function is applied, the window function is preferably a non-negative smooth bell-shaped curve, for example a Cauchy-Lorentz function.

The determination of the fit envelope signal function represents an idealized curve progression of the envelope signal curve with the object to exclude any pulse variation caused by ventilation or respiration induced heart-lung interaction.

The difference between the envelope signal curve and the fit envelope signal function reflects a modulation which is due to the respiration or ventilation of the patient. Thus, a respiratory pulse variation signal corresponding to the pulse variations caused by the respiration of the patient is determined. Preferably, the respiratory pulse variation signal is determined in such a way that the respiratory pulse variation signal oscillates around an average value thereof. Preferably, the area defined by the lower part of the curve of the respiratory pulse variation signal, i.e. the area below the average value, substantially corresponds to the area defined by the upper part of the curve of the respiratory pulse variation signal, i.e. the area above the average value.

The absolute respiratory pulse variation curve may correspond to an envelope respiration curve, in which case the fit respiration function might also be regarded as a fit envelope respiration function. The fit respiration function may then represent an idealized curve progression of the envelope respiration curve over the plurality of respiratory cycles. The determination of the envelope respiration curve, which might in that case correspond to the second data values, is based on the previously determined respiratory pulse variation signal. Preferably, the envelope respiration curve is calculated by continuously determining a distance dimension of the respiratory pulse variation signal from an average thereof and by thereafter preferably applying a low pass filter to the distance dimension. Preferably, the low pass filter has a cutoff frequency below the respiration frequency of the patient. In other words, the portion below the average value of the oscillating curve of respiratory pulse variation signal is preferably folded up to the upper portion. Then, the resulting curve is preferably flattened by using a low pass filter having a cutoff frequency below the respiration frequency of the patient. The curve can be flattened in such a way that the area below the flattened curve remains unchanged as compared to the area under the non-flattened curve. Optionally, the flattened curve may additionally be multiplied by a predetermined value. If the flattened curve is multiplied, for example, with the value of the square root of 2, the finally obtained envelope respiration curve substantially is at the level of the upper extremes in amplitude of the respiratory pulse variation signal. Preferably, the average value, which is used as the basis of the distance dimension calculation, of the respiratory pulse variation signal is determined as moving average over a period of one single respiration cycle of the patient or by applying a low pass filter on the respiratory pulse variation signal, e.g. an elliptic or butterworth filter.

In an embodiment, the absolute respiratory pulse variation curve does not correspond to an envelope respiration curve, but to a different curve indicative of absolute values of the respiratory pulse variation signal. That is to say, it may be preferred that the fit respiration function is determined without first determining an envelope respiration curve for the previously determined respiratory pulse variation signal and then determining the fit respiration function based on the envelope respiration curve. Instead, it may be preferred to determine the fit respiration function by fitting the second functional prototype to data values, i.e. second data values, corresponding to a different kind of an absolute respiratory pulse variation signal, i.e. to data values derived differently from the respiratory pulse variation signal. Nevertheless, such different kind of preprocessing might involve one or more of the steps described above with respective to the determination of the envelope respiration curve from the respiratory pulse variation signal. In an embodiment the absolute respiratory pulse variation curve, which may correspond to the second data values, is determined by considering absolute values of respective differences between the respiratory pulse variation signal and the average. These absolute values may then correspond to the second data values. Hence, in particular, the fit respiration function may be determined by considering absolute values of respective differences between the respiratory pulse variation signal and the average, thereby folding the portion of the respiratory pulse variation signal below an average value thereof up to the upper portion, and by fitting the second functional prototype to the so obtained values.

In case the fit respiration function is determined by first determining an envelope respiration curve for the previously determined respiratory pulse variation signal and by then determining the fit respiration function based on the envelope respiration curve, in order to avoid any bias from the calculatory steps involved, the envelope respiration curve is preferably calculated analogously to the envelope signal curve, but is associated with the respiratory pulse variation signal instead of the measured pulse signal. More generally, the fit respiration function is preferably calculated based on the data values, i.e. the second data values, to which it is to be fitted, i.e. the envelope respiration curve or the data values derived differently from the respiratory pulse variations signal, for instance, analogously to the fit envelope signal function, with the exception that the data values to which it is to be fitted are different, namely are associated with the respiratory pulse variation signal instead of the measured pulse signal. That is, for example, if the Cauchy-Lorentz function is used as functional prototype to determine the fit envelope signal function, also the Cauchy-Lorentz function is preferably used as functional prototype to determine the fit respiration function.

If the physiological parameter is indicative of, or corresponds to, a patient's volume or fluid responsiveness, the indicator that is representative for the physiological parameter can be determined based on the fit envelope signal function and the fit respiration function. Preferably, the indicator that is representative for the physiological parameter is determined based on at least one parameter of the fit envelope signal function and at least one parameter of the fit respiration function. For example, an indicator that is representative for a patient's volume responsiveness can be determined based on a ratio between a maximum of the fit envelope signal function and a maximum of the fit respiration function. Such a ratio, or a function of this ratio, particularly its inverse, can represent an appropriate indicator that is representative for the patient's volume responsiveness.

In a further aspect of the present invention a method for determining an indicator that is representative for a physiological parameter is presented, wherein the method comprises:

providing a measured pulse signal of a patient over a time period corresponding to a plurality of subsequent respiratory cycles of the patient by a pulse signal providing unit, wherein the pulse signal is a pressure signal that has been measured by using a pressure cuff with a pressure sensor being in contact with the outer skin of the patient, wherein pressure applied to the patient by the pressure cuff is increased or decreased, while the pressure sensor measures the pressure signal on the outer skin of the patient, and wherein the measured pressure is indicative of blood pulsations, carrying out a determination procedure adapted to determine an indicator that is representative for a physiological parameter based on the provided pulse signal by an indicator determination unit, wherein the determination procedure includes a) determining a respiratory pulse variation signal corresponding to pulse variations caused by ventilation or respiration induced heart-lung interaction based on the provided measured pulse signal, b) determining a systolic part of the respiratory pulse variation signal, which corresponds to a time period in which the increasing or decreasing applied pressure passed the systolic arterial pressure of the patient and which therefore is prone to comprising an artifact, c) modifying the respiratory pulse variation signal such that the determined systolic part of the respiratory pulse variation signal is corrected and d) determining the indicator based on the measured pulse signal and the modified respiratory pulse variation signal.

In another aspect of the present invention a computer program for determining an indicator that is representative for a physiological parameter is presented, wherein the computer program comprises program code means for causing an apparatus as defined by any of claims 1 to 17 to carry out the steps of the method as defined in claim 18.

It shall be understood that the apparatus of claim 1, the method of claim 18 and the computer program of claim 19, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
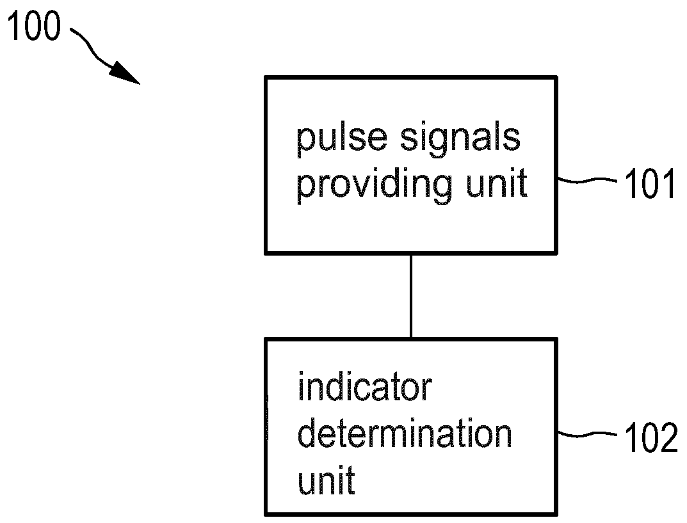
FIG. 1 shows schematically and exemplarily an apparatus for determining an indicator that is representative for a physiological parameter.
Figure 2:
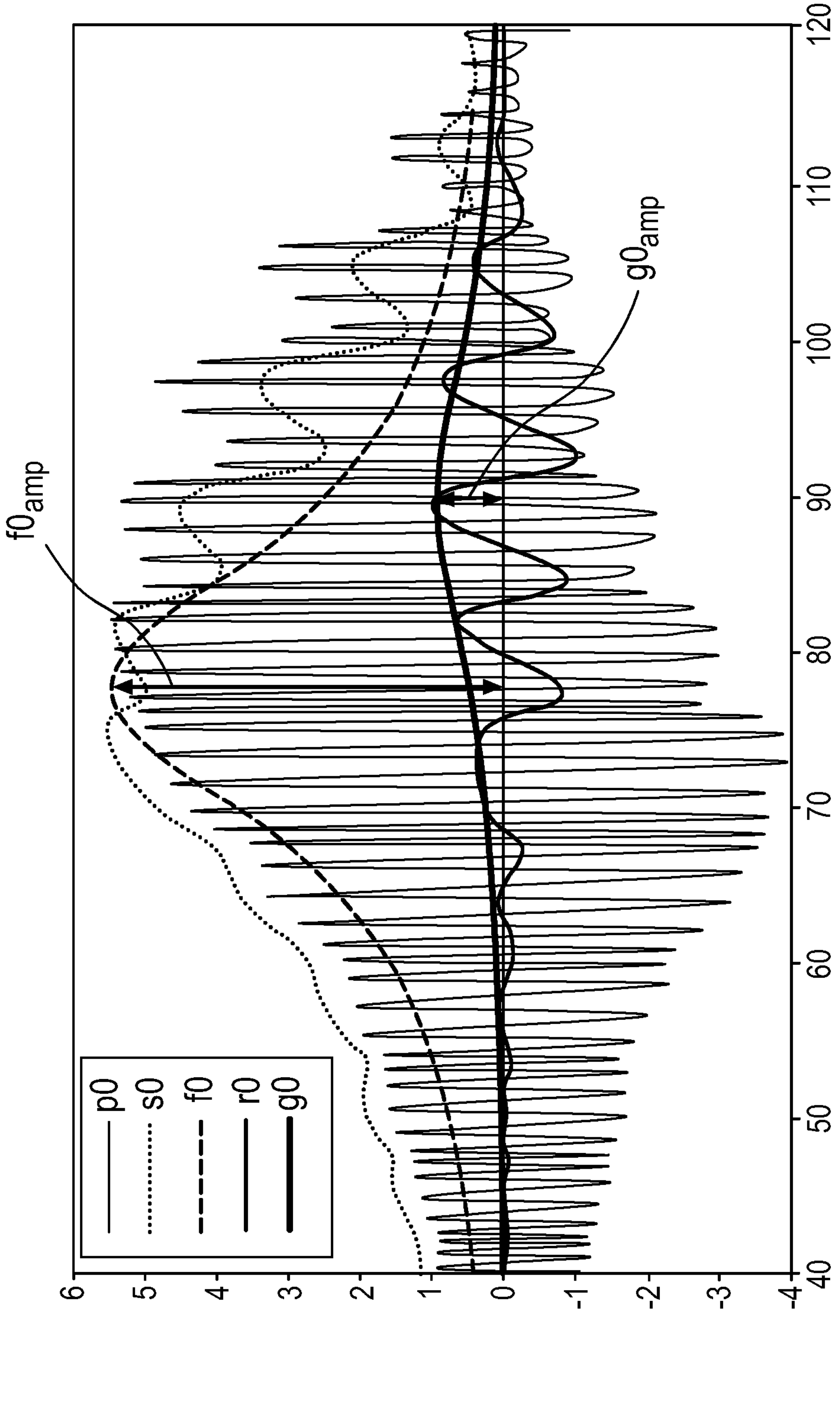
FIG. 2 shows schematically and exemplarily several curves which depend on applied pressure which has been applied by using a pressure cuff.

FIG. 1 shows schematically and exemplarily an apparatus 100 for determining an indicator that is representative for a physiological parameter. The apparatus 100 comprises a pulse signal providing unit 101 configured to provide a measured pulse signal with a sequence of pulses of a patient over a time period corresponding to a plurality of subsequent respiratory cycles of the patient. The measured pulse signal has been detected by a non-invasive pulse measurement method. The apparatus 100 further comprises an indicator determination unit 102 configured to carry out a determination procedure adapted to determine an indicator that is representative for a physiological parameter based on the provided sequence of pulse signal. The determination procedure includes determining a respiratory pulse variation signal corresponding to pulse variations caused by ventilation or respiration induced heart-lung interaction based on the provided measured pulse signal. The respiratory pulse variation signal preferentially is represented as a respiratory pulse variation signal r0 oscillating around an average value thereof as illustrated in FIG. 2. For instance, the respiratory pulse variation signal can be represented as a respiratory pulse variation signal r0 oscillating around an average value thereof by subtracting the average value from the initially determined respiratory pulse variation signal.

Moreover, preferentially the pulse signal providing unit 101 is configured such that also the measured pulse signal is represented as pulse signal p0 oscillating around an average value thereof, wherein the indicator determination unit 102 is configured such that first data values s0 are determined by determining an envelope signal curve for the pulse signal p0. For instance, the pulse signal can be represented as a pulse signal p0 oscillating around an average value thereof by subtracting the average value from the initially provided measured pulse signal.

The first data values s0 can be determined, for instance, by considering only the absolute values of the pulse signal p0, which would correspond to folding up the pulse signal p0. The first data values s0 can also be determined by calculating the square of the pulse signal p0. Moreover, it is possible to determine the first data values by clipping the pulse signal p0, i.e. by only considering the positive values of the pulse signal p0. Preferentially, the first data values s0 are also filtered. For instance, the first data values s0 can be filtered by using a low pass filter, particularly an elliptic low pass filter. In a preferred embodiment, the first data values s0 are filtered by using an elliptic forward-backward IIR low pass filter of fourth order. It can have, for instance, a cut-off frequency of about 0.3 Hz and a filter attenuation of 30 dB per decade. In a preferred embodiment, the filtered first data values s0 form the envelope signal curve for the pulse signal p0.

Moreover, the indicator determination unit 102 is configured to, in a first fitting, fit a provided first functional prototype, which depends on a first fit parameter to be modified during the first fitting, to the first data values s0 such that a resulting fit envelope signal function f0 represents an idealized curve progression of the envelope signal curve over the plurality of respiratory cycles without comprising pulse variations caused by ventilation or respiration induced heart-lung interaction. The indicator determination unit 102 can be configured such that a), before the fitting, the number of data values s0 is reduced for the entire fitting, and/or b) an initial value is determined for the fit parameter based on characteristics of the data values s0 which are related to characteristics of the functional prototype and/or based on a value of the fit parameter known from a previous fitting, and/or c) the fitting is carried out in several stages, wherein the number of data values s0 used for the fitting is increased from stage to stage and wherein in a current stage a value of a fit parameter determined in a previous stage is used as initial value for the fit parameter in the current stage.

As indicated in FIG. 1, the apparatus 100 may comprise a connection between the pulse signal providing unit 101 and the indicator determination unit 102 via which the pulse signal providing unit 101 can provide the measured pulse signal to the indicator determination unit 102.

FIG. 2 illustrates schematically and exemplarily how an indicator that is representative for a patient's volume responsiveness can be determined based on a provided measured pulse signal with pulses that have been detected using a pressure cuff, wherein the pressure applied in the pressure cuff is continuously increased in the course of the measurement period. The horizontal axis of the graph shown in FIG. 2 indicates the pressure applied in the pressure cuff, and could therefore also be viewed as a time axis. The vertical axis indicates a pressure measured by the pressure sensor of the pressure cuff. The measured pulse signal is represented, as mentioned above, as pulse signal p0 oscillating around an average value thereof. As also mentioned above, based on the pulse signal p0, data values s0 are determined by determining an envelope signal curve for the pulse signal p0, wherein the data values s0 may be regarded as being, or being values of, the envelope signal curve. The functional prototype provided for fitting is in this case a bell-shaped Cauchy-Lorentz function of the form $$f(x) = \frac{f_{amp}}{1 + \left(\frac{x - f_{max}}{f_{bw}}\right)^2}, \tag{1}$$

wherein x is the pressure or time indicated on the horizontal axis, the parameter $f_{amp}$ is decisive for the amplitude of the bell-shaped curve of the functional prototype, the parameter $f_{max}$ is decisive for the location of the maximum on the time-axis or pressure-axis and the parameter $f_{bw}$ is decisive for the width at half maximum. Fitting this functional prototype, which is in this case considered as a first functional prototype, to the determined envelope signal curve s0 results in a fit envelope signal function f0, which represents an idealized curve progression of the envelope signal curve s0 over the plurality of respiratory cycles in the measurement period without comprising pulse variations caused by ventilation or respiration induced heart-lung interaction.

By taking the difference between the envelope signal curve s0 and the fit envelope signal function f0, the respiratory pulse variation signal corresponding to the pulse variations caused by ventilation or respiration induced heart-lung interaction over the plurality of respiratory cycles are determined, wherein, like the pulse signal p0, also the respiratory pulse variation signal is represented as a respiratory pulse variation signal r0 oscillating around an average value thereof. Also the respiratory pulse variation signal r0 may be filtered. The filtering may use, for instance, high pass filter, particularly a Butterworth high pass filter. The Butterworth high pass filter might be defined by being of the third order, having a cut-off frequency of about 0.5 Hz and being applied back and forth. However, also another filter might be used for filtering the respiratory pulse variation signal r0. It is also possible that the respiratory pulse variation signal is not filtered.

Then, in analogy to how the envelope signal curve s0 was determined from the pulse signal p0, an envelope respiration curve is determined by determining an envelope curve for the previously determined respiratory pulse variation signal r0. A second functional prototype $$g(x) = \frac{g_{amp}}{1 + \left(\frac{x - g_{max}}{g_{bw}}\right)^2}, \tag{2}$$

which is in this case of the same bell-shaped Cauchy-Lorentz type as the first functional prototype, is provided. In particular, x is again the pressure or time indicated on the horizontal axis, the parameter $g_{amp}$ is decisive for the amplitude of the bell-shaped curve of the functional prototype, the parameter $g_{max}$ is decisive for the location of the maximum on the time-axis or pressure-axis and the parameter $g_{bw}$ is decisive for the width at half maximum. By fitting the second functional prototype to the previously determined envelope respiration curve, a fit envelope respiration function g0 is determined, which represents an idealized curve progression of the envelope respiration curve over the plurality of respiratory cycles in the measurement period. Instead of determining an envelope respiration curve for the respiratory pulse variation signal r0 and fitting the second functional prototype to the envelope respiration curve, it may be preferred to fit the second functional prototype to data values derived more directly from the respiratory pulse variation signal r0, i.e., for instance, by considering absolute values of respective differences between the respiratory pulse variation signal and its average, thereby folding up the portion below the average value up to the upper portion. Hence, the fit envelope respiration function g0 might be understood more generally as a fit respiration function g0.

Finally, an indicator that is representative for the patient's volume responsiveness is determined as the ratio between the value $g0_{amp}$ of the parameter $g_{amp}$ for the fit respiration function g0 and the value $f0_{amp}$ of the parameter $f_{amp}$ for the fit envelope signal function f0, i.e.

$$F0 = \frac{g0_{amp}}{f0_{amp}}. \tag{3}$$

Conventionally, the pulse pressure variation is calculated by $$PPV = \frac{PP_{max} - PP_{min}}{\frac{1}{2}(PP_{max} + PP_{min})}, \quad (4)$$

wherein $PP_{max}$ and $PP_{min}$ are the maximal and minimal pulse pressure, respectively, within one single respiratory cycle. Hence, it estimates a magnitude of pulse variations caused by the patient's respiration. In the procedure described above with reference to FIG. 2, the magnitude of the pulse variations caused by the patient's respiration is represented by the parameter $g0_{amp}$. Similar to the calculation of the pulse pressure variation according to above equation (4) as indicator for the patient's volume responsiveness, the parameter $g0_{amp}$ is "normalized" in equation (3), namely by division through $f0_{amp}$, which indicates a magnitude of the pulse variations caused by heart beats. Therefore, the volume responsiveness indicator obtained according to equation (3) may also be viewed as being indicative for the conventional indicator obtained according to equation (4). Differences might arise from the circumstance that the procedure leading to equation (3) does not rely on single maximum/minimum values of measured pulse pressure variations corresponding to one single heartbeat, but instead takes all pulses measured in the measurement time into account.

The determination procedure described above with reference to FIG. 2 is an example of a determination procedure used for determining an indicator that is representative for a physiological parameter—in this case a patient's volume responsiveness. In order to improve the determination of the indicator, the respiratory pulse variation signal r0 is modified as it will be explained in the following.

Figure 3:
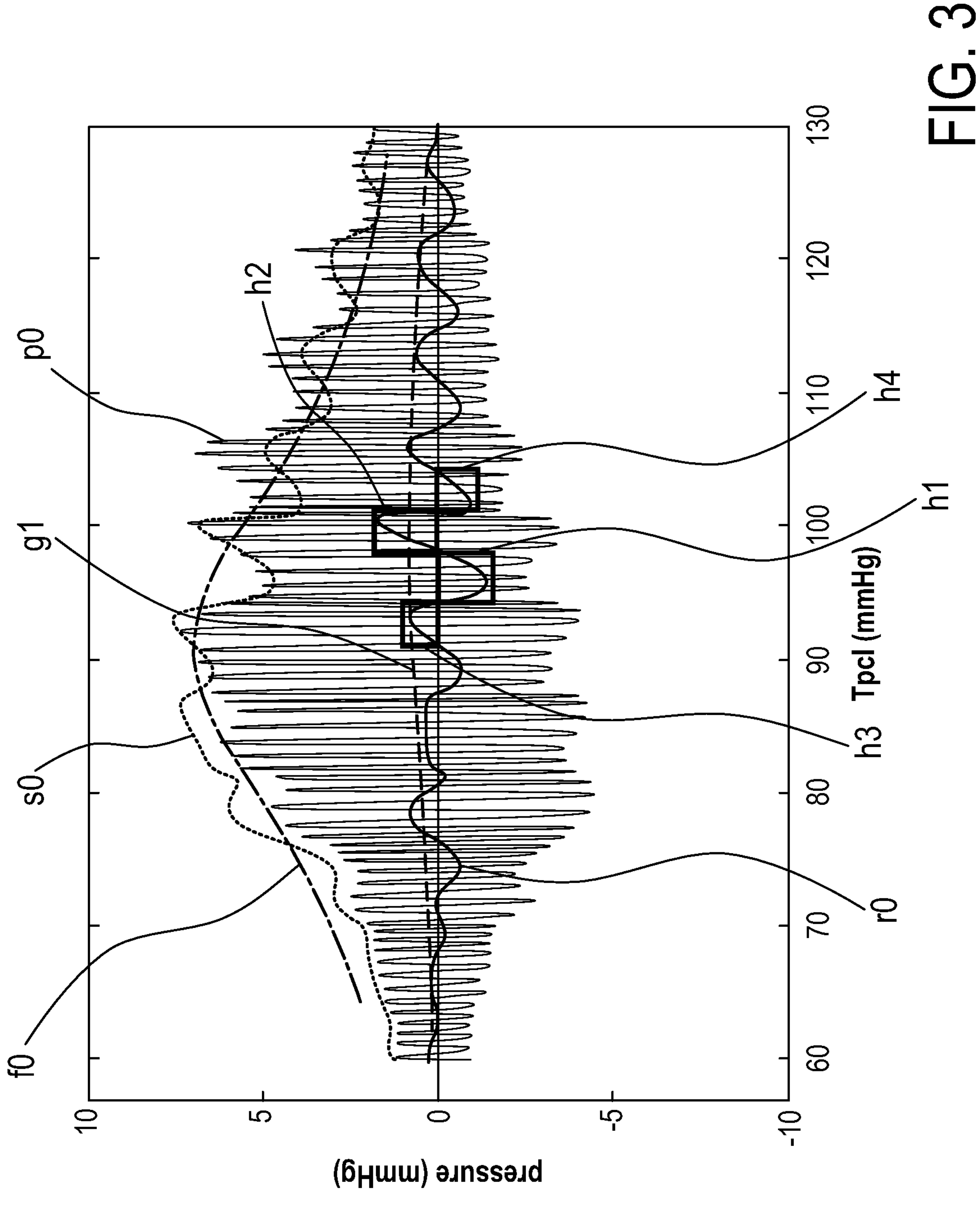
FIG. 3 shows schematically and exemplarily several curves which depend on applied pressure which has been applied by using a pressure cuff, wherein a respiratory pulse variation curve is modified in accordance with a first modification procedure.

The indicator determination unit 102 is configured to modify the respiratory pulse variation signal r0 by replacing a half wave h1, h2 of the respiratory pulse variation signal r0 by an adjacent half wave h3, h4 of the respiratory pulse variation signal r0. In particular, the indicator determination unit 102 is configured such that the replacing includes determining a half wave h1 of the respiratory pulse variation signal r0 with a lowest minimum, determining a half wave h2 of the respiratory pulse variation signal r0 with a highest maximum and replacing the temporally first one of the lowest minimum half wave h1 and the highest maximum half wave h2 by a half wave h3 before and adjacent to the first one and replacing the respective temporally second one of the lowest minimum half wave h1 and the highest maximum half wave h2 by a half wave h4 behind and adjacent to the temporally second one. Thus, a) respiration half waves h1, h2 with maximal amplitude, i.e. maximum and minimum, are detected, b) these two respiration half waves h1, h2 are deleted, c) the respiration half wave h3 in tissue clamping pressure directly before the first deletion area is duplicated and added to its own end, and d) the respiration half wave h4 in tissue clamping pressure directly after the second deletion area is duplicated and added to its own start. The respiration half waves h1, h2, h3, h4 are schematically and exemplarily illustrated in FIG. 3. The fit respiration function, which is determined by using the modified respiratory pulse variation signal r1, is indicated in FIG. 3 as g1. It is noted that FIGS. 2 and 3 are based on different initial measured pulse signals with sequences of pulses and therefore the curves look different.

Figure 4:
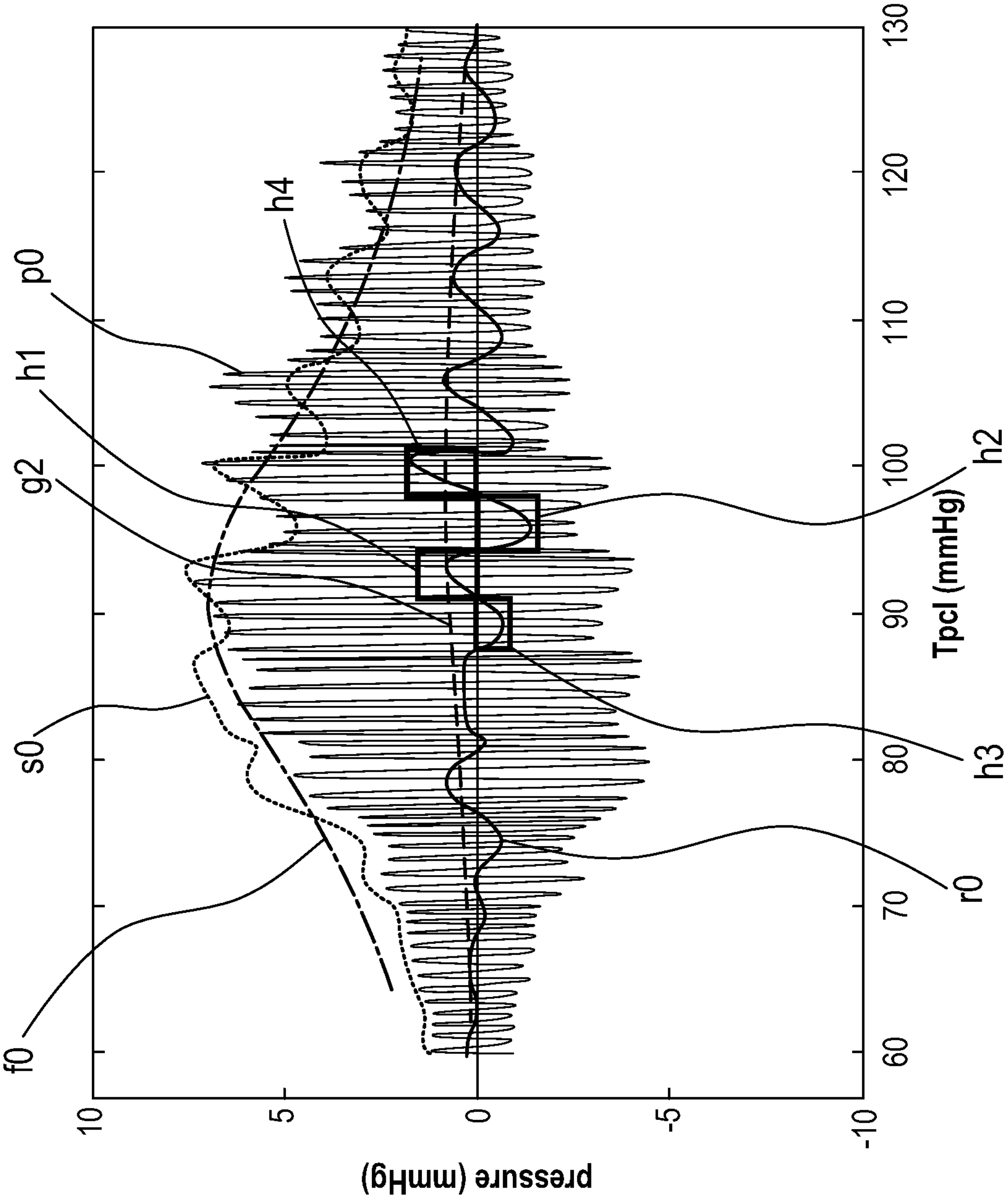
FIG. 4 shows schematically and exemplarily several curves which depend on applied pressure which has been applied by using a pressure cuff, wherein a respiratory pulse variation curve is modified in accordance with a second modification procedure.

The indicator determination unit 102 can also be configured such that the replacing includes a) determining a half wave h2 of the respiratory pulse variation signal r0 with a lowest minimum, b) replacing the lowest minimum half wave h2 by a half wave h4 behind and adjacent to the lowest minimum half wave h2 and replacing the half wave h1 before and adjacent to the lowest minimum half wave h2 by a half wave h3 before and adjacent to this half wave h1 to be replaced. Thus, a) a negative respiration half wave h2 with maximal amplitude, i.e. a minimum, is detected, b) this respiration half wave h2 and the, in tissue clamping pressure, directly preceding half wave h1 are deleted, c) the respiration half wave h3 directly before the first deletion area is duplicated and added to its own end, and d) the respiration half wave h4 directly after the second deletion area is duplicated and added to its own start. The respiration half waves h1, h2, h3, h4 are schematically and exemplarily illustrated in FIG. 4. The fit respiration function, which is determined by using the modified respiratory pulse variation signal r2, is indicated in FIG. 4 as g2. It is noted that also FIGS. 2 and 4 are based on different initial measured pulse signals with sequences of pulses and therefore the curves look different.

The indicator determination unit 102 can be configured to determine the indicator based on at least one first ratio F1, F2 of a maximum of a respective fit respiration function g1, g2 and the maximum of the fit envelope signal function f0, which is named modified first ratio because of being based on the respective modified pulse variation signal, and/or a second ratio S0 of a) the fit respiration function g0 at the maximum of the fit envelope signal function f0 and b) the maximum of the fit envelope signal function f0, which is named unmodified second ratio because of being based on the unmodified respiratory pulse variation signal. In particular, the indicator determination unit 102 is configured to determine the indicator based on a combination of a respective ratio and a square of the respective ratio, wherein the combination to be used for determining a respective indicator can be determined by calibration. In an embodiment, a fluid responsiveness parameter (FRP) can be defined as follows:

$$FRP = \left(flag0\cdot\left(d1\cdot S0^2 + d2\cdot S0 + k0\right) + flag1\cdot\left(d3\cdot F1^2 + d4\cdot F1 + k1\right) + flag2\cdot\left(d5\cdot F2^2 + d6\cdot F2 + k2\right)\right)/(d7\cdot flag0 + flag1 + d9\cdot flag2). \quad (5)$$

In an embodiment, in equation (5), i) S0 could be replaced by F0 and/or ii) F1 could be replaced by S1 and/or iii) F2 could be replaced by S2. In a preferred embodiment the fluid responsiveness parameters PPVni, SVVni and SPVni are defined as follows:

$$PPVni = \left(flag3\cdot\left(c1\cdot S0^2 + c2\cdot S0 + b0\right) + flag4\cdot\left(c3\cdot F1^2 + c4\cdot F1 + b1\right) + flag5\cdot\left(c5\cdot F2^2 + c6\cdot F2 + b2\right)\right)/(c7\cdot flag3 + c8\cdot flag4 + c9\cdot flag5), \quad (6)$$

-continued $$SVVni = \left(flag6\cdot\left(c10\cdot S0^2 + c11\cdot S0 + b4\right) + flag7\cdot\left(c12\cdot F1^2 + c13\cdot F1 + b5\right)\right) / \left(c14\cdot flag6 + c15\cdot flag7\right), \quad (7)$$

$$SPVni = \left(flag8\cdot\left(c16\cdot S0^2 + c17\cdot S0 + b6\right) + flag9\cdot\left(c18\cdot F1^2 + c19\cdot F1 + b7\right) + flag10\cdot\left(c20\cdot F2^2 + c21\cdot F2 + b8\right)\right) / \left(c22\cdot flag8 + c23\cdot flag9 + c24\cdot flag10\right). \quad (8)$$

Thus, in a preferred embodiment, the indicator determination unit 102 is configured to determine the indicator based on A) multiplying the square of the second unmodified ratio S0 with a first factor d1; c1; c10; c16 for calculating a first product, multiplying the second unmodified ratio S0 with a second factor d2; c2; c11, c17 for calculating a second product, adding the first and second products and a summand k0; b0; b4; b6 for calculating a first subindicator, and/or B) multiplying the square of the first modified ratio F1 with a third factor d3; c3; c12; c18 for calculating a third product, multiplying the first modified ratio F1 with a fourth factor d4; c4; c13; c19 for calculating a fourth product and adding the third and fourth products and a summand k1; b1; b5; b7 for calculating a second subindicator, and/or C) multiplying the square of the first modified ratio F2 with a fifth factor d5; c5; c20 for calculating a fifth product, multiplying the first modified ratio F2 with a sixth factor d6; c6; c21 for calculating a sixth product and adding the fifth and sixth products and a summand k2; b2; b8 for calculating a third subindicator, and D) combining the determined subindicators. The combining preferentially includes weighting the determined subindicators and adding the weighted subindicators. The weighting is indicated in equations (5) to (8) by the respective divisors.

As explained above, the parameters, i.e. here the parameters c1 . . . c24 and b0 . . . b8 and above the parameters d1 . . . d9 and k0 . . . k2, used for determining the respective indicator are determined by calibration. Thus, these parameters are predetermined such that, during a calibration phase, deviations between very accurately measured invasive indicators and the indicators obtained by using equation (5) or by using equations (6), (7), (8), respectively, are minimized.

The flags flag0 . . . flag 10 each can either be zero or one. In particular, the indicator determination unit 102 is configured to set a respective flag to one, if a predefined characteristic of the respective corresponding fit respiration function fulfils a respective predefined condition. The predefined characteristic and the corresponding predefined condition can be defined by calibration. For instance, the predefined characteristic can be a maximum of the respective corresponding fit respiration function and the predefined condition can be that it should be smaller than a predefined threshold, wherein the predefined threshold can be determined by calibration. In a further example, the predefined characteristic can be the argument of the maximum of the respective corresponding fit respiration function and the predefined condition can be that this argument should be within predefined limits. Thus, the indicator determination unit 102 can be configured to set a respective flag to one if the argument of a maximum of the respective corresponding fit respiration function is within predetermined limits. Also, these predefined limits can be predefined by calibration.

Moreover, in an embodiment, the indicator determination unit can be adapted to output a predefined value like, for instance, 2 percent, if all flags are set to zero. In an embodiment, the indicator determination unit also can be adapted to output, for a respective indicator, a predefined value like, for instance, 2 percent, if the respective indicator has been determined to be negative.

Preferentially, for determining PPV, the pulse signal p0 initially has been folded up for determining the first data values s0 which are then used in the further steps. Moreover, preferentially, for determining SVV, the pulse signal p0 initially has been squared for determining the first data values s0 which are then used in the further steps. Furthermore, preferentially, for determining SPV, the pulse signal p0 initially has been clipped for determining the first data values s0 which are then used in the further steps.

Figure 5:
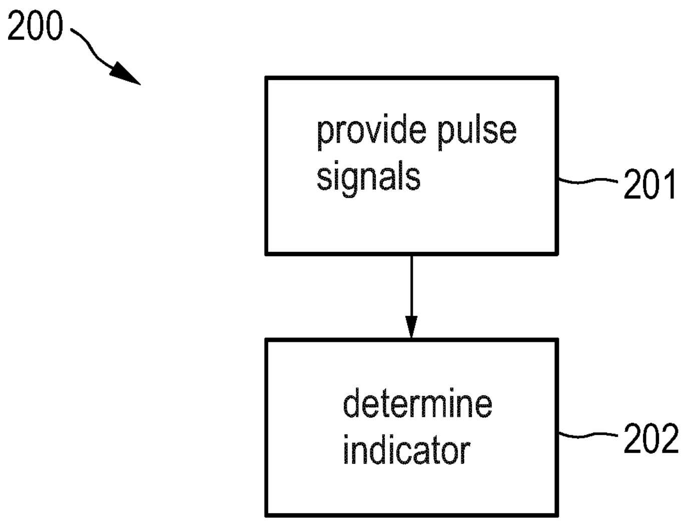
FIG. 5 shows a flow chart exemplarily illustrating a method for determining an indicator that is representative for a physiological parameter.

FIG. 5 illustrates schematically and exemplarily an embodiment of a method 200 for determining an indicator that is representative of a physiological parameter, such as a patient's volume responsiveness. The method comprises, in a first part 201, providing a measured pulse signal with a sequence of pulses of a patient over a time period corresponding to a plurality of subsequent respiratory cycles of the patient by a pulse signal providing unit 101, wherein the provided measured pulse signal has been detected by a non-invasive pulse measurement method. The measurement might be performed using a pressure cuff, wherein the pressure applied in the pressure cuff is continuously increased or decreased in the course of a measurement period. In a second part 202, the method 200 comprises carrying out a determination procedure adapted to determine an indicator that is representative for the physiological parameter based on the provided measured pulse signal with the sequence of pulses by an indicator determination unit 102, wherein the determination procedure includes a) determining a respiratory pulse variation signal r0 corresponding to pulse variations caused by ventilation or respiration induced heart-lung interaction based on the provided measured pulse signal and modifying the respiratory pulse variation signal r0 by replacing a half wave h1, h2 of the respiratory pulse variation signal r0 by an adjacent half wave h3, h4 of the respiratory pulse variation signal r0 and b) determining the indicator based on the measured pulse signal and the modified respiratory pulse variation signal.

In an example, the indicator determination unit 102 can be configured to consider the maximum of the half wave h1 of the technique yielding F2 and the maximum of the respiratory pulse variation signal r0, when determining the indicator. In particular, the indicator determination unit 102 can be configured to determine the indicator such that the influence of F1 to the determination of the indicator decreases with increasing ratio Mh1/Mr0, wherein Mh1 is the maximum of the half wave h1 of the technique yielding F2, i.e. the technique described above with reference to FIG. 4, and Mr0 is the maximum of the respiratory pulse variation signal r0. The indicator determination unit 102 can be configured to especially consider this ratio when determining FRP. In particular, in an example, in equation (5) the term flag1·(d3·F1$^2$+d4·F1+k1) can be modified depending on the ratio Mh1/Mr0 as follows:

If Mh1/Mr0 is larger than a first percentage perc_upper, in the above mentioned term F1 is replaced by F2. This first percentage preferentially is within a range from 90% to 100% and further preferred 97%.

If Mh1/Mr0 is smaller than a second percentage perc_lower, with perc_lower being smaller than perc_upper, the above mentioned term and hence F1 are unchanged. This second percentage preferentially is within a range from 80% to 95% and further preferred 92%.

If Mh1/Mr0 is smaller or equal to perc_upper and larger or equal to perc_lower (perc_upper≥Mh1/Mr0≥perc_lower), in the above mentioned term F1 is replaced by a weighted average of F1 and F2 with a weighting that depends on Mh1/Mr0, preferentially F1 is replaced by F1+(Mh1/Mr0−perc_lower)/(perc_upper−perc_lower)*(F2−F1).

In a further example, the indicator determination unit can be configured to determine FRP in accordance with following rewritten equation (5):

$$FRP = \big(flag0 \cdot d7 \cdot (d1/d7 \cdot S0^2 + d2/d7 \cdot S0 + k0/d7) + flag1 \cdot d8 \cdot (d3/d8 \cdot F1^2 + d4/d8 \cdot F1 + k1/d8) + flag2 \cdot d9 \cdot (d5/d9 \cdot F2^2 + d6/d9 \cdot F2 + k2/d9)\big) / (d7 \cdot flag0 + d8 \cdot flag1 + d9 \cdot flag2),$$

wherein the weighting factor d8 is adjusted by multiplying it with a factor adj_factor, which is based on the ratio Mh1/Mr0. In an example, the factor adj_factor is defined as follows. If Mh1/Mr0 is larger than perc_upper, the factor adj_factor is zero. If Mh1/Mr0 is smaller than perc_lower, the factor adj_factor is one. If perc_upper is larger than or equal to Mh1/Mr0 and if perc_lower is smaller than or equal to Mh1/Mr0 (perc_upper≥Mh1/Mr0≥perc_lower), the factor adj_factor is a value between zero and one, wherein the factor adj_factor preferentially depends on Mh1/Mr0. It particularly depends linearly on Mh1/Mr0. For instance, the factor adj_factor can be (Mh1/Mr0−perc_upper)/(perc_lower−perc_upper).

Figure 6:
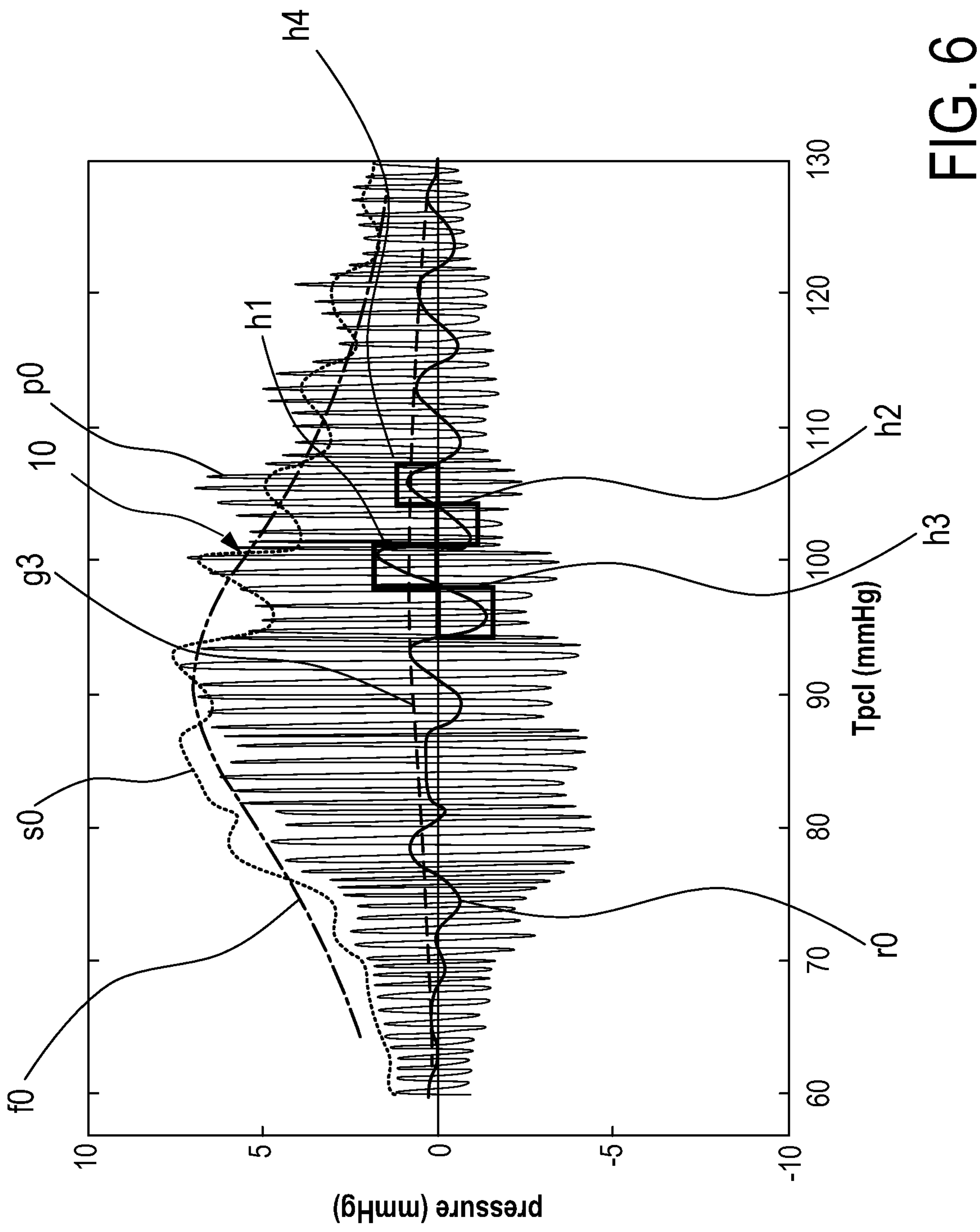
FIG. 6 shows schematically and exemplarily several curves which depend on applied pressure which has been applied by using a pressure cuff, wherein a respiratory pulse variation curve is modified in accordance with a third modification procedure.

The indicator determination unit 102 can also be configured to determine the systolic part of the respiratory pulse variation signal r0 as a part in which a maximum decrease position 10 is present, at which the respiratory pulse variation signal r0 and/or the envelope signal curve s0 of the pulse signal p0 has its maximum decrease. In an embodiment the indicator determination unit 102 is configured to modify the respiratory pulse variation signal r0 by a) replacing the half wave h1, which comprises the maximum immediately before the maximum decrease position 10, and the half wave h2, which comprises the minimum immediately behind the maximum decrease position 10, by half waves h3, h4 of another part the respiratory pulse variation signal. The respiration half waves h1, h2, h3, h4 are schematically and exemplarily illustrated in FIG. 6. The fit respiration function, which is determined by using the modified respiratory pulse variation signal r3, is indicated in FIG. 6 as g3. It is noted that also FIGS. 2 and 6 are based on different initial measured pulse signals with sequences of pulses and therefore the curves look different.

For example, following steps can be carried out: a) the maximum decrease position 10 is determined, b) the half wave h1, which comprises the maximum immediately before the maximum decrease position 10, and the half wave h2, which comprises the minimum immediately behind the maximum decrease position 10, are determined, c) these two half waves h1 and h2 are deleted, d) the respiration half wave h3 directly before the first deletion area is duplicated and added to its own end, and e) the respiration half wave h4 directly behind the second deletion area is duplicated and added to its own start.

The previously described technique for determining the systolic part of the respiratory pulse variation signal and the modification of the respiratory pulse variation signal, which are based on the maximum decrease position, can be combined with the further techniques described above, in order to determine an indicator being indicative of a physiological parameter. For example, FRP can be determined in accordance with following equation:

$$FRP = \big(flag0 \cdot (a1 \cdot S0^2 + a2 \cdot S0 + e0) + flag1 \cdot (a3 \cdot F1^2 + a4 \cdot F1 + e1) + flag2 \cdot (a5 \cdot F2^2 + a6 \cdot F2 + e2) + (flag11 + a7 \cdot F3^2 + a8 \cdot F3 + e3)\big) / (a9 \cdot flag0 + a10 \cdot flag1 + a11 \cdot flag2 + a12 \cdot flag11). \quad (9)$$

In an embodiment, similar to what has been described above with respect to equation (5), i) S0 could be replaced by F0 and/or ii) F1 could be replaced by S1 and/or iii) F2 could be replaced by S2. Moreover, F3 could be replaced by S3.

F3 is comparable to F2, i.e. it is a first ratio of a maximum of the fit respiration function g3 and the maximum of the fit envelope signal function f0, which, as explained above, is named modified first ratio because of being based on the modified pulse variation signal. S3 is comparable to S2, i.e. it is a second ratio of a) the fit respiration function g3 at the maximum of the fit envelope signal function f0 and b) the maximum of the fit envelope signal function f0, wherein S3 is named modified second ratio because of being based on the modified respiratory pulse variation signal.

The fluid responsiveness parameters PPVni and SPVni can be defined as follows:

$$PPVni = \big(flag3 \cdot (f1 \cdot S0^2 + f2 \cdot S0 + u0) + flag4 \cdot (f3 \cdot F1^2 + f4 \cdot F1 + u1) + flag5 \cdot (f5 \cdot F2^2 + f6 \cdot F2 + u2) + flag12 \cdot (f7 \cdot F3^2 + f8 \cdot F3 + u3)\big) / (f9 \cdot flag3 + f10 \cdot flag4 + f11 \cdot flag5 + f12 \cdot flag12), \quad (10)$$

$$SPVni = \big(flag8 \cdot (f13 \cdot S0^2 + f14 \cdot S0 + u4) + flag9 \cdot (f15 \cdot F1^2 + f16 \cdot F1 + u5) + flag10 \cdot (f17 \cdot F2^2 + f18 \cdot F2 + u6) + flag13 \cdot (f19 \cdot F3^2 + f20 \cdot F3 + u7)\big) / (f21 \cdot flag8 + f22 \cdot flag9 + f23 \cdot flag10 + f24 \cdot flag13). \quad (11)$$

In a further example, the result of the maximum decrease position technique can be used for exchanging the term containing F2 in above equations (5), (6) and (8). Thus, the indicator determination unit 102 can be configured to determine one or several indicators being indicative of physiological parameters in accordance with following equations:

$$FRP = \big(flag0 \cdot (v1 \cdot S0^2 + v2 \cdot S0 + i0) + flag1 \cdot (v3 \cdot F1^2 + v4 \cdot F1 + i1) + flag2 \cdot (v5 \cdot F3^2 + v6 \cdot F3 + i2)\big) / (v7 \cdot flag0 + v8 \cdot flag1 + v9 \cdot flag2). \quad (12)$$

$$PPVni = \big(flag3 \cdot (j1 \cdot S0^2 + j2 \cdot S0 + l0) + flag4 \cdot (j3 \cdot F1^2 + j4 \cdot F1 + l1) + flag5 \cdot (j5 \cdot F3^2 + j6 \cdot F3 + l2)\big) / j7 \cdot flag3 + j8 \cdot flag4 + j9 \cdot flag5), \quad (13)$$

-continued $$SPVni = \left(flag8\cdot\left(j10\cdot S0^2 + j11\cdot S0 + l3\right) + flag9\cdot\left(j12\cdot F1^2 + j13\cdot F1 + l4\right) + flag10\cdot\left(j14\cdot F3^2 + j15\cdot F3 + l5\right)\right) / j16\cdot flag8 + j17\cdot flag9 + j18\cdot flag10\right). \tag{14}$$

Although in above described examples, particularly with reference to equation (7), the fluid responsiveness parameter SVVni is determined without considering F2, in an embodiment the indicator determination unit 102 can be configured to determine the fluid responsiveness parameter SVVni by considering also F2. For instance, it can be determined in accordance with following equation:

$$SVVni = \left(flag6\cdot\left(m1\cdot S0^2 + m2\cdot S0 + n0\right) + flag7\cdot\left(m3\cdot F1^2 + m4\cdot F1 + n1\right) + flag14\cdot\left(m5\cdot F2^2 + m6\cdot F2 + n2\right)\right) / m7\cdot flag6 + m8\cdot flag7 + m9\cdot flag14). \tag{15}$$

The indicator determination unit 102 can also be configured to determine the fluid responsiveness parameter SVVni by also considering F3, for instance, in accordance with following equation:

$$SVVni = \left(flag6\cdot\left(o1\cdot S0^2 + o2\cdot S0 + w0\right) + flag7\cdot\left(o3\cdot F1^2 + o4\cdot F1 + w1\right) + flag14\cdot\left(o5\cdot F2^2 + o6\cdot F2 + w2\right) + flag15\cdot\left(o7\cdot F3^2 + o8\cdot F3 + w3\right)\right) / (o9\cdot flag6 + o10\cdot flag7 + o11\cdot flag14 + o12\cdot flag15). \tag{16}$$

The fluid responsiveness parameter SVVni can also be determined by replacing F2 by F3 in equation (15). Thus, the indicator determination unit 102 can be configured to determine the fluid responsiveness parameter SVVni in accordance with following equation:

$$SVVni = flag6\cdot\left(q1\cdot S0^2 + q2\cdot S0 + t0\right) + flag7\cdot\left(q3\cdot F1^2 + q4\cdot F1 + t1\right) + flag15\cdot\left(q5\cdot F3^2 + q6\cdot F3 + t2\right)\right) / (q7\cdot flag6 + q8\cdot flag7 + q9\cdot flag15). \tag{17}$$

Also regarding the further equations (9) to (17), the parameters, i.e. the respective parameters a1 . . . a12, e0 . . . e3, f1 . . . f24, u0 . . . u7, v1 . . . v9, i0 . . . i2, j1 . . . j18, l0 . . . l5, m1 . . . m9, n0 . . . n2, o1 . . . o12, w0 . . . w3, q1 . . . q9 and t0 . . . t2, used for determining the respective indicator are determined by calibration. Thus, these parameters of a respective equation are predetermined such that, during a calibration phase, a deviation between a respective very accurately measured invasive indicator and the respective indicator obtained by using a respective one of the equations is minimized.

Moreover, also regarding the further equations (9) to (17) the flags, i.e. flag0 . . . flag15, each can either be zero or one. In particular, the indicator determination unit 102 can be configured to set a respective flag to one, if a predefined characteristic of the respective corresponding fit respiration function fulfils a respective predefined condition. The predefined characteristic and the corresponding predefined condition can be defined by calibration. For instance, also regarding these equations the predefined characteristic can be a maximum of the respective corresponding fit respiration function and the predefined condition can be that it should be smaller than a predefined threshold, wherein the predefined threshold can be determined by calibration. In a further example, the predefined characteristic can be the argument of the maximum of the respective corresponding fit respiration function and the predefined condition can be that this argument should be within predefined limits. Thus, the indicator determination unit 102 can be configured to set a respective flag to one if the argument of a maximum of the respective corresponding fit respiration function is within predetermined limits. Also, these predefined limits can be predefined by calibration.

Moreover, also regarding equations (9) to (17), in an embodiment the indicator determination unit can be adapted to output a predefined value like, for instance, 2 percent, if all flags are set to zero. In an embodiment, the indicator determination unit also can be adapted to output, for a respective indicator, a predefined value like, for instance, 2 percent, if the respective indicator has been determined to be negative.

In an example the indicator determination unit 102 is configured to determine the systolic part of the respiratory pulse variation signal r0 as a part in which a difference between a maximum and a following, i.e. directly following, minimum of the respiratory pulse variation signal r0 is largest. Thus, the indicator determination unit 102 can be configured to determine the differences between a respective maximum and a directly following respective minimum of the respiratory pulse variation signal for the pairs of maxima and directly following minima of the respiratory pulse variation signal and to determine, among the determined differences, the largest difference, in order to determine the systolic part of the respiratory pulse variation signal, i.e. in this embodiment the two half waves of the respiratory pulse variation signal for which the difference between a maximum of a first one of the two half waves and a minimum of a second, directly following one of the two half waves is largest. The indicator determination unit 102 can be configured to modify the respiratory pulse variation signal r0 by a) replacing the half wave h1, which comprises the maximum, and the half wave h2, which comprises the minimum, by half waves h3, h4 of another part of the respiratory pulse variation signal.

Thus, also following steps can be carried out: a) the largest difference between a maximum of the respiratory pulse variation signal and a directly following minimum of the respiratory pulse variation signal can be determined, b) the half wave h1, which comprises the determined maximum, and the half wave h2, which comprises the determined minimum, can be deleted, c) the respiration half wave h3, directly before the first deletion area can be duplicated and added to its own end, and d) the respiration half wave h4 directly behind the second deletion area can be duplicated and added to its own start.

The respiration half waves h1, h2, h3, h4 of the previously described maximum-minimum technique are also schematically and exemplarily illustrated in FIG. 6. Hence, the systolic part h1, h2, which is schematically and exemplarily in FIG. 6, can be determined a) by determining the maximum decrease of the respiratory pulse variation signal r0 and/or of the envelope signal curve s0 of the pulse signal p0, as described further above, or b) by determining the largest difference between a maximum of the respiratory pulse variation signal and a directly following minimum of the respiratory pulse variation signal.

Although in above embodiments the apparatus 100 has been described as being an apparatus for determining certain indicators like, for instance, indicators being representative for a patient's volume responsiveness, in the same or other embodiments the apparatus may also be an apparatus for determining an indicator that is representative for another physiological parameter. Moreover, although in the above described embodiments the functional prototype is a bell-shaped function, other functional prototypes may be used. For instance, the functional prototype may be provided depending on a type of the detected pulse signal based on which the data values are determined to which the functional prototype is to be fitted.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the providing of the measured pulse signal, the determining of the data values based on the provided pulse signal, the fitting of the provided respective functional prototype to the determined data values, the determining of the indicator, et cetera, performed by one or several units or devices can be performed by any other number of units or devices. These procedures can be implemented as program code means of a computer program and/or as dedicated hardware, particularly as an embedded system.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope. In the claims, the reference signs, which should not be construed as limiting the scope, are included in brackets like, for example, r0, h1, h2, h3, h4, g1, g2, g3, et cetera.

The invention relates to an apparatus for determining an indicator, which is representative for a physiological parameter of a patient like, for instance, a fluid responsiveness parameter, based on a pulse signal. The apparatus determines a) a respiratory pulse variation signal corresponding to pulse variations caused by ventilation or respiration induced heart-lung interaction based on the pulse signal and b) a systolic part of the respiratory pulse variation signal, which corresponds to a time period in which an increasing or decreasing applied pressure passed the systolic arterial pressure of the patient and which therefore is prone to comprising an artifact. Moreover, the respiratory pulse variation signal is modified such that the determined systolic part of the respiratory pulse variation signal is corrected, wherein the indicator is determined based on the measured pulse signal and the modified respiratory pulse variation signal. This procedure allows for a more accurate determination of the indicator.

The invention claimed is:

1. An apparatus for determining an indicator that is representative for a physiological parameter, wherein the apparatus comprises:

a pulse signal provider configured to provide a measured pulse signal of a patient over a time period corresponding to a plurality of subsequent respiratory cycles of the patient, wherein the pulse signal is a pressure signal that has been measured by using a pressure cuff with a pressure sensor being in contact with the outer skin of the patient, wherein pressure applied to the patient by the pressure cuff is increased or decreased, while the pressure sensor measures the pressure signal on the outer skin of the patient, and wherein the measured pressure is indicative of blood pulsations, an indicator determiner configured to carry out a determination procedure adapted to determine an indicator that is representative for a physiological parameter based on the provided pulse signal, wherein the determination procedure includes: (a) determining a respiratory pulse variation signal (r0) corresponding to pulse variations caused by ventilation or respiration induced heart-lung interaction based on the provided measured pulse signal, (b) determining a systolic part of the respiratory pulse variation signal (r0), which corresponds to a time period in which the increasing or decreasing applied pressure passed the systolic arterial pressure of the patient and which therefore is prone to comprising an artifact, (c) modifying the respiratory pulse variation signal (r0) such that the determined systolic part of the respiratory pulse variation signal (r0) is corrected and (d) determining the indicator based on the measured pulse signal and the modified respiratory pulse variation signal (r0).

2. The apparatus as defined by claim 1, wherein the indicator determiner is configured to correct the systolic part of the respiratory pulse variation signal (r0) by replacing at least a subpart of the systolic part by another part of the respiratory pulse variation signal (r0) and/or by removing at least a subpart of the systolic part.

3. The apparatus as defined by claim 1, wherein the indicator determiner is configured to represent the respiratory pulse variation signal (r0) as a respiratory pulse variation signal (r0) oscillating around an average value thereof and to determine the systolic part of the respiratory pulse variation signal (r0) such that it includes a lowest minimum and/or a highest maximum of the respiratory pulse variation signal (r0).

4. The apparatus as defined by claim 3, wherein the indicator determiner is configured to determine the systolic part of the respiratory pulse variation signal (r0) such that it includes a half wave of the respiratory pulse variation signal (r0) with a lowest minimum and/or a half wave of the respiratory pulse variation signal (r0) with a highest maximum and to modify the respiratory pulse variation signal (r0) by a) replacing the lowest minimum half wave and/or the highest maximum half wave by a half wave of another part the respiratory pulse variation signal (r0) and/or b) removing the lowest minimum half wave and/or the highest maximum half wave.

5. The apparatus as defined by claim 4, wherein the indicator determiner is configured to determine the systolic part of the respiratory pulse variation signal (r0) such that it includes at least one first half wave of the respiratory pulse variation signal (r0) adjacent the half wave of the respiratory pulse variation signal (r0) with the lowest minimum and/or at least one second half wave of the respiratory pulse variation signal (r0) adjacent the half wave of the respiratory pulse variation signal (r0) with the highest maximum and to modify the respiratory pulse variation signal (r0) by a) replacing the at least one first half wave and/or the at least one second half wave by a half wave of another part of the respiratory pulse variation signal (r0) and/or b) removing the at least one first half wave and/or the at least one second half wave.

6. The apparatus as defined by claim 5, wherein the indicator determiner is configured to determine the systolic part of the respiratory pulse variation signal (r0) such that it includes a half wave of the respiratory pulse variation signal (r0) with a lowest minimum and a half wave of the respiratory pulse variation signal (r0) with a highest maximum and to modify the respiratory pulse variation signal (r0) by replacing the temporally first one of the lowest minimum half wave and the highest maximum half wave by a half wave before and adjacent to the first one and replacing the respective temporally second one of the lowest minimum half wave and the highest maximum half wave by a half wave behind and adjacent to the temporally second one.

7. The apparatus as defined by claim 5, wherein the indicator determiner is configured to determine the systolic part of the respiratory pulse variation signal (r0) such that it includes a half wave of the respiratory pulse variation signal (r0) with a lowest minimum and the half wave before and adjacent to the lowest minimum half wave and to modify the respiratory pulse variation signal (r0) by replacing the lowest minimum half wave by a half wave behind and adjacent to the lowest minimum half wave and replacing the half wave before and adjacent to the lowest minimum half wave by a half wave before and adjacent to this half wave to be replaced.

8. The apparatus as defined by claim 1, wherein the indicator determiner is configured to determine the systolic part of the respiratory pulse variation signal (r0) as a part in which a maximum decrease position is present, at which the respiratory pulse variation signal (r0) and/or an envelope signal curve (s0) of the pulse signal (p0) has its maximum decrease.

9. The apparatus as defined by claim 8, wherein the indicator determiner is configured to represent the respiratory pulse variation signal (r0) as a respiratory pulse variation signal (r0) oscillating around an average value thereof and to modify the respiratory pulse variation signal (r0) by: (a) replacing the half wave (h1), which comprises the maximum immediately before the maximum decrease position, and the half wave (h2), which comprises the minimum immediately behind the maximum decrease position, of the respiratory pulse variation signal (r0) by half waves (h3, h4) of another part the respiratory pulse variation signal and/or (b) removing these half waves (h1, h2).

10. The apparatus as defined by claim 1, wherein the indicator determiner is configured to determine the systolic part of the respiratory pulse variation signal (r0) as a part in which a difference between two consecutive extrema of the respiratory pulse variation signal (r0) is largest.

11. The apparatus as defined by claim 10, wherein the indicator determiner is configured to represent the respiratory pulse variation signal (r0) as a respiratory pulse variation signal (r0) oscillating around an average value thereof and to modify the respiratory pulse variation signal (r0) by: (a) replacing the half waves, which comprise the consecutive extrema with the largest difference by half waves of another part the respiratory pulse variation signal and/or (b) removing these half waves.

12. The apparatus as defined by claim 1, wherein the pulse signal provider is configured to represent the measured pulse signal as pulse signal (p0) oscillating around an average value thereof, wherein the indicator is configured to represent the respiratory pulse variation signal (r0) as a respiratory pulse variation signal (r0) oscillating around an average value thereof and to represent the modified respiratory pulse variation signal as a modified respiratory pulse variation signal oscillating around an average value thereof, and wherein the indicator determiner is configured such that first data values (s0) are determined by determining an envelope signal curve for the pulse signal (p0), in a first fitting, a provided first functional prototype, which depends on a first fit parameter to be modified during the first fitting, is fitted to the first data values (s0) such that a resulting fit envelope signal function (f0) represents an idealized curve progression of the envelope signal curve over the plurality of respiratory cycles without comprising pulse variations caused by ventilation or respiration induced heart-lung interaction, second data values are determined by determining an absolute respiratory pulse variation curve for the modified respiratory pulse variation signal, in a second fitting, a provided second functional prototype, which depends on a second fit parameter to be modified during the second fitting, is fitted to the second data values such that a resulting fit respiration function (g1, 92, g3) is indicative of an idealized progression in amplitude of the absolute respiratory pulse variation curve over the plurality of respiratory cycles, and the indicator is determined based on the fit envelope signal function (f0) and the fit respiration function (g1, g2, g3).

13. The apparatus as defined by claim 12, wherein the indicator determiner is configured such that the determined respiratory pulse variation signal (r0) corresponds to a difference between the envelope signal curve (s0) and the fit envelope signal function (f0).

14. The apparatus as defined by claim 12, wherein the indicator determiner is configured to determine the indicator based on a first ratio (F1, F2, F3) of a maximum of the fit respiration function (g1, g2, g3) and the maximum of the fit envelope signal function (f0), which is named modified first ratio because of being based on the modified respiratory pulse variation signal, and/or based on a second ratio (S1, S2, S3) of: (a) the fit respiration function (g1, 92, g3) at the maximum of the fit envelope signal function (f0) and (b) the maximum of the fit envelope signal function (f0), which is named modified second ratio because of being based on the modified respiratory pulse variation signal.

15. The apparatus as defined by claim 12, wherein the indicator determiner is configured to carry out the steps of determining the second data values and of fitting, in the second fitting, the provided second functional prototype resulting in a fit respiration function (90) for the unmodified respiratory pulse variation signal (r0) and to determine the indicator further based on a second ratio (S0) of: (a) the fit respiration function (g0), which has been determined based on the unmodified respiratory pulse variation signal, at the maximum of the fit envelope signal function (f0) and (b) the maximum of the fit envelope signal function (f0), which is named unmodified second ratio because of being based on the unmodified respiratory pulse variation signal, and/or based on a first ratio (F0) of a maximum of the fit respiration function (g0), which has been determined based on the unmodified respiratory pulse variation signal, and the maximum of the fit envelope signal function (f0), which is named unmodified first ratio because of being based on the unmodified respiratory pulse variation signal.

16. The apparatus as defined by claim 14, wherein the indicator determiner is configured to determine the indicator based on a combination of a respective ratio (F0, F1, F2, F3, S0, S1, S2, S3) and a square of a respective ratio (F0, F1, F2, F3, S0, S1, S2, S3).

17. The apparatus as defined by claim 14, wherein the indicator determiner is configured to determine the indicator by A) multiplying the square of the second unmodified ratio (S0) or of the first unmodified ratio (F0) with a first factor (c1; c10; c16; d1; a1; f1; f13; v1; j1; j10; m1; o1; q1) for calculating a first product, multiplying the second unmodified ratio (S0) or the first unmodified ratio (F0), respectively, with a second factor (c2; c11; c17; d2; a2; f2; f14; v2; j2; j11; m2; o2; q2) for calculating a second product, adding the first and second products and a summand (b0; b4; b6; k0; e0; u0; u4; i0; l0; l3; n0; w0; t0) for calculating a first subindicator, and/or B) carrying out the steps of determining the second data values and of fitting, in the second fitting, a provided second functional prototype resulting in the fit respiration function (g1) as defined in claim 12 and carrying out the steps of determining the first modified ratio (F1) or the second modified ratio (S1) as defined in claim 14 for the respiratory pulse variation signal (r1) which has been modified as defined in claim 6, multiplying the square of the first modified ratio (F1) or of the second modified ratio (S1), respectively, with a third factor (c3; c12; c18; d3; a3; f3; f15; v3; j3; j12; m3; o3; q3) for calculating a third product, multiplying the first modified ratio (F1) or the second modified ratio (S1), respectively, with a fourth factor (c4; c13; c19; d4; a4; f4; f16; v4; j4; j13; m4; o4; q4) for calculating a fourth product and adding the third and fourth products and a summand (b1; b5; b7; k1; e1; u1; u5; i1; l1; l4; n1; w1; t1) for calculating a second subindicator, and/or C) carrying out the steps of determining the second data values and of fitting, in the second fitting, a provided second functional prototype resulting in the fit respiration function (g2) as defined in claim 12 and carrying out the steps of determining the first modified ratio (F2) as defined in claim 14 for the respiratory pulse variation signal (r2) which has been modified as defined in claim 7, multiplying the square of the first modified ratio (F2) or of the second modified ratio (S2) with a fifth factor (c5; c20; d5; a5; f5; f17; m5; o5) for calculating a fifth product, multiplying the first modified ratio (F2) or the second modified ratio (S2), respectively, with a sixth factor (c6; c21; d6; a6; f6; f18; m6; o6) for calculating a sixth product and adding the fifth and sixth products and a summand (b2; b8; k2; e2; u2; u6; n2; w2) for calculating a third subindicator, and/or D) carrying out the steps of determining the second data values and of fitting, in the second fitting, a provided second functional prototype resulting in the fit respiration function (g3) as defined in claim 12 and carrying out the steps of determining the first modified ratio (F3) as defined in claim 14 for the respiratory pulse variation signal (r3) which has been modified as defined in claim 9, multiplying the square of the first modified ratio (F3) or of the second modified ratio (S3) with a seventh factor (a7; f7; f19; v5; j5; j14; o7; q5) for calculating a seventh product, multiplying the first modified ratio (F3) or the second modified ratio (S3), respectively, with an eighth factor (a8; f8; f20; v6; j6; j15; o8; q6) for calculating an eighth product and adding the seventh and eighth products and a summand (e3; u3; u7; i2; l2; l5; w3; t2) for calculating a fourth subindicator, and/or E) combining the determined subindicators.

18. A method for determining an indicator that is representative for a physiological parameter, wherein the method comprises:

providing) a measured pulse signal of a patient over a time period corresponding to a plurality of subsequent respiratory cycles of the patient by a pulse signal provider, wherein the pulse signal is a pressure signal that has been measured by using a pressure cuff with a pressure sensor being in contact with the outer skin of the patient, wherein pressure applied to the patient by the pressure cuff is increased or decreased, while the pressure sensor measures the pressure signal on the outer skin of the patient, and wherein the measured pressure is indicative of blood pulsations, carrying out a determination procedure adapted to determine an indicator that is representative for a physiological parameter based on the provided pulse signal by an indicator determiner, wherein the determination procedure includes a) determining a respiratory pulse variation signal (r0) corresponding to pulse variations caused by ventilation or respiration induced heart-lung interaction based on the provided measured pulse signal, b) determining a systolic part of the respiratory pulse variation signal, which corresponds to a time period in which the increasing or decreasing applied pressure passed the systolic arterial pressure of the patient and which therefore is prone to comprising an artifact, c) modifying the respiratory pulse variation signal such that the determined systolic part of the respiratory pulse variation signal is corrected and d) determining the indicator based on the measured pulse signal and the modified respiratory pulse variation signal.

19. A tangible non-transitory computer readable storage medium that stores a computer program, wherein the computer program, when executed by a processor, causes a computer apparatus to to carry out the steps of:

providing a measured pulse signal of a patient over a time period corresponding to a plurality of subsequent respiratory cycles of the patient by a pulse signal provider, wherein the pulse signal is a pressure signal that has been measured by using a pressure cuff with a pressure sensor being in contact with the outer skin of the patient, wherein pressure applied to the patient by the pressure cuff is increased or decreased, while the pressure sensor measures the pressure signal on the outer skin of the patient, and wherein the measured pressure is indicative of blood pulsations, carrying out a determination procedure adapted to determine an indicator that is representative for a physiological parameter based on the provided pulse signal by an indicator determiner, wherein the determination procedure includes a) determining a respiratory pulse variation signal (r0) corresponding to pulse variations caused by ventilation or respiration induced heart-lung interaction based on the provided measured pulse signal, b) determining a systolic part of the respiratory pulse variation signal, which corresponds to a time period in which the increasing or decreasing applied pressure passed the systolic arterial pressure of the patient and which therefore is prone to comprising an artifact, c) modifying the respiratory pulse variation signal such that the determined systolic part of the respiratory pulse variation signal is corrected and d) determining the indicator based on the measured pulse signal and the modified respiratory pulse variation signal.

* * * * *